(12) United States Patent
Herzog et al.

(10) Patent No.: US 12,031,558 B2
(45) Date of Patent: Jul. 9, 2024

(54) TITANIUM DIOXIDE COMPOSITE INSULATOR ARTIFICIAL MUSCLE

(71) Applicant: TOYOTA MOTOR ENGINEERING & MANUFACTURING NORTH AMERICA, INC., Plano, TX (US)

(72) Inventors: Max Herzog, Ann Arbor, MI (US); Maduran Palaniswamy, Ann Arbor, MI (US); Michael P. Rowe, Pinckney, MI (US); Charles R. Rutledge, Tipton, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 238 days.

(21) Appl. No.: 17/529,531

(22) Filed: Nov. 18, 2021

(65) Prior Publication Data

US 2023/0149186 A1    May 18, 2023

(51) Int. Cl.
*F15B 15/10* (2006.01)

(52) U.S. Cl.
CPC ...... *F15B 15/103* (2013.01); *F15B 2215/305* (2013.01)

(58) Field of Classification Search
CPC .......................... F15B 15/103; F15B 2214/305
See application file for complete search history.

(56) References Cited

U.S. PATENT DOCUMENTS

| 5,505,321 | A | * | 4/1996 | Caron | ................. | H05K 3/4691 |
| | | | | | | 428/209 |
| 6,016,217 | A | | 1/2000 | Dotzel et al. | | |

(Continued)

FOREIGN PATENT DOCUMENTS

| CN | 111102264 A | * | 5/2020 | ............. F15B 15/10 |
| KR | 1613485 B1 | | 4/2016 | |
| WO | 2017/031712 A1 | | 3/2017 | |

OTHER PUBLICATIONS

Kellaris et al., Peano-HASEL actuators: Muscle-mimetic, electrohydraulic transducers that linearly contract on activation, Science Robotics, Jan. 31, 2018, vol. 3, Issue 14 (Year: 2018).*
E. Acome, et al. "Hydraulically Amplified Self-Healing Electrostatic Actuators With Muscle-Like Performance"; Science Jan. 5, 2018: vol. 359, Issue 6371, pp. 61-65.

*Primary Examiner* — Kenneth Bomberg
*Assistant Examiner* — Daniel S Collins
(74) *Attorney, Agent, or Firm* — Dinsmore & Shohl LLP

(57) ABSTRACT

An artificial muscle includes a housing including an electrode region and an expandable liquid region and a dielectric liquid housed within the housing. The artificial muscle further includes an electrode pair positioned in the electrode region of the housing, the electrode pair comprising a first electrode and a second electrode, wherein the electrode pair is configured to actuate between a non-actuated state and an actuated state such that actuation from the non-actuated state to the actuated state directs the dielectric liquid into the expandable liquid region, expanding the expandable liquid region. The artificial muscle also includes a composite electrical insulating layered structure in contact with at least one of the first electrode or the second electrode, wherein the composite electrical insulating layered structure that includes an electrical insulator layer surrounded by adhesive surfaces. The adhesive surfaces are located between one or more flexible electrical insulators.

20 Claims, 12 Drawing Sheets

(56) References Cited

U.S. PATENT DOCUMENTS

| | | |
|---|---|---|
| 10,381,547 B2 | 8/2019 | Takamatsu et al. |
| 11,009,487 B2 | 5/2021 | Fan et al. |
| 2009/0206702 A1 | 8/2009 | Kawakubo et al. |

* cited by examiner

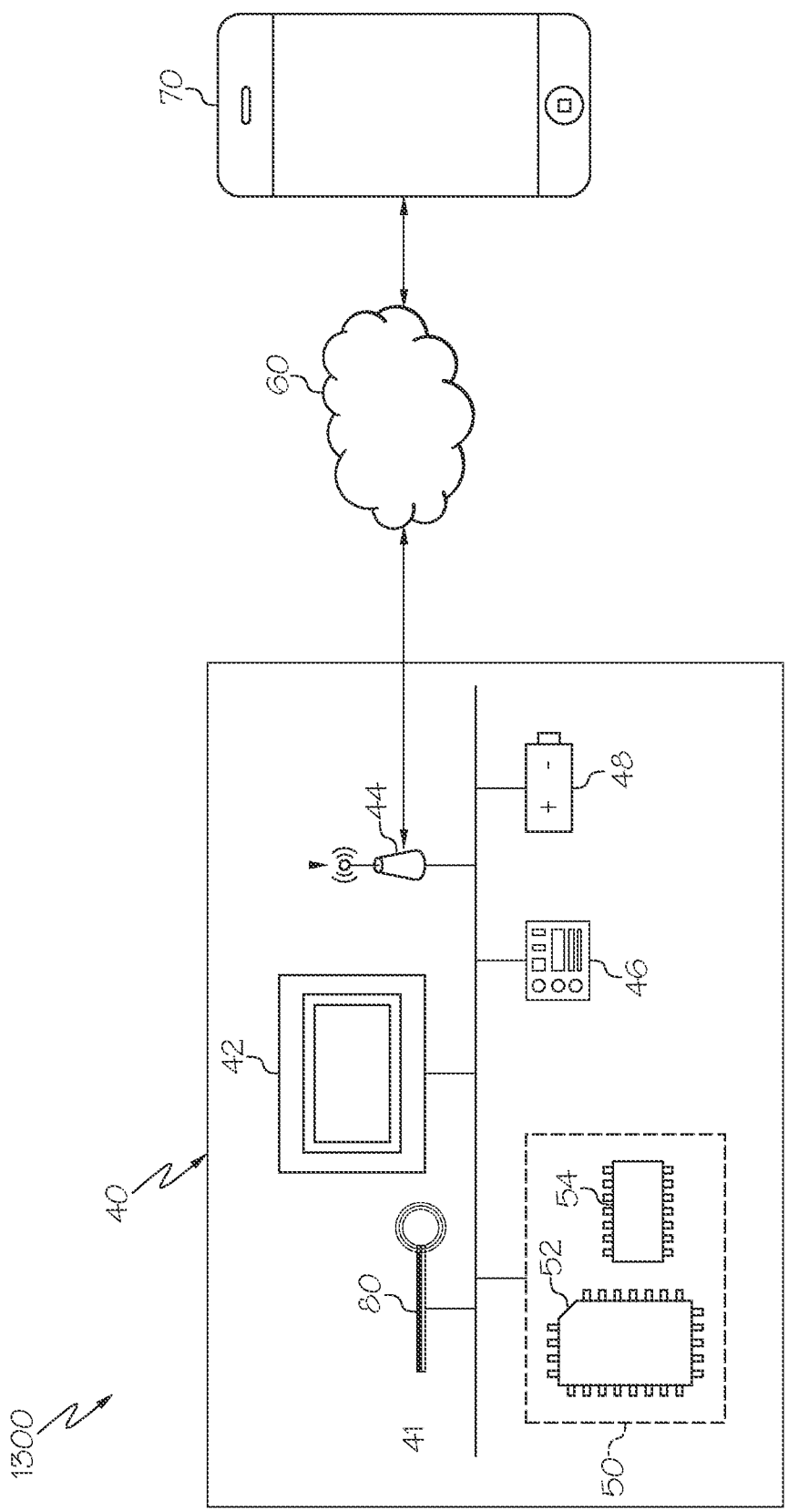

TITANIUM DIOXIDE COMPOSITE INSULATOR ARTIFICIAL MUSCLE

TECHNICAL FIELD

The present specification generally relates to artificial muscles and, in particular, to artificial muscles utilizing nanoparticle composite electrical insulators.

BACKGROUND

Artificial muscles attempt to mimic the versatility, performance, and reliability of biological muscles. Some artificial muscles rely on fluidic actuators, but fluidic actuators require a supply of pressurized gas or liquid and fluid transport must occur through systems of channels and tubes, limiting the speed and efficiency. Other artificial muscles use thermally activated polymer fibers, but these are difficult to control and operate at low efficiencies. Moreover, in order to exert increasing amounts of force, current attempts at artificial muscles often require bulky actuators and/or increasing their operating voltage.

Accordingly, there exists a need to create more force output with the same size actuator and the same operating voltage.

SUMMARY

In one embodiment, an artificial muscle includes a housing including an electrode region and an expandable liquid region. The artificial muscle also includes a dielectric liquid housed within the housing. The artificial muscle further includes an electrode pair positioned in the electrode region of the housing, the electrode pair including a first electrode and a second electrode, wherein the electrode pair is configured to actuate between a non-actuated state and an actuated state such that actuation from the non-actuated state to the actuated state directs the dielectric liquid into the expandable liquid region, expanding the expandable liquid region. The artificial muscle additionally includes a composite electrical insulating layered structure in contact with at least one of the first electrode or the second electrode. The composite electrical insulating layered structure includes an electrical insulator layer surrounded by adhesive surfaces. The composite electrical insulating layered structure also includes adhesive surfaces located between one or more flexible electrical insulators. The composite electrical insulating layered structure further includes one or more flexible electrical insulators of which at least one is directly affixed to one of the first electrode and the second electrode.

In another embodiment, an artificial muscle includes a housing including an electrode region and an expandable liquid region. The artificial muscle also includes a dielectric liquid housed within the housing. The artificial muscle further includes an electrode pair positioned in the electrode region of the housing, the electrode pair including a first electrode and a second electrode, wherein the electrode pair is configured to actuate between a non-actuated state and an actuated state such that actuation from the non-actuated state to the actuated state directs the dielectric liquid into the expandable liquid region, expanding the expandable liquid region. The artificial muscle additionally includes composite electrical insulating layered structure in contact with at least one of the first electrode or the second electrode. The composite electrical insulating layered structure includes a plurality of electrical insulator nanoparticles located within a subset of an adhesive surface. The composite electrical insulating layered structure also includes the adhesive surface located between one or more flexible electrical insulators. The composite electrical insulating layered structure further includes one or more flexible electrical insulators of which at least one is directly affixed to one of the first electrode and the second electrode.

In a further embodiment, an artificial muscle includes a housing including an electrode region and an expandable liquid region. The artificial muscle also includes a dielectric liquid housed within the housing. The artificial muscle further includes an electrode pair positioned in the electrode region of the housing, the electrode pair including a first electrode and a second electrode, wherein the electrode pair is configured to actuate between a non-actuated state and an actuated state such that actuation from the non-actuated state to the actuated state directs the dielectric liquid into the expandable liquid region, expanding the expandable liquid region. The artificial muscle additionally includes composite electrical insulating layered structure in contact with at least one of the first electrode or the second electrode. The composite electrical insulating layered structure includes an electrical insulator layer including titanium dioxide nanoparticles, wherein the electrical insulator layer has a thickness in a range of 10-15 μm and is surrounded by acrylic adhesives. The composite electrical insulating layered structure also includes the acrylic adhesives located between one or more biaxially oriented polypropylene films. The composite electrical insulating layered structure further includes one or more biaxially oriented polypropylene films of which at least one is directly affixed to one of the first electrode and the second electrode.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 13 schematically depicts an actuation system for operating an artificial muscle, according to one or more embodiments shown and described herein.

DETAILED DESCRIPTION

Figure 1A:
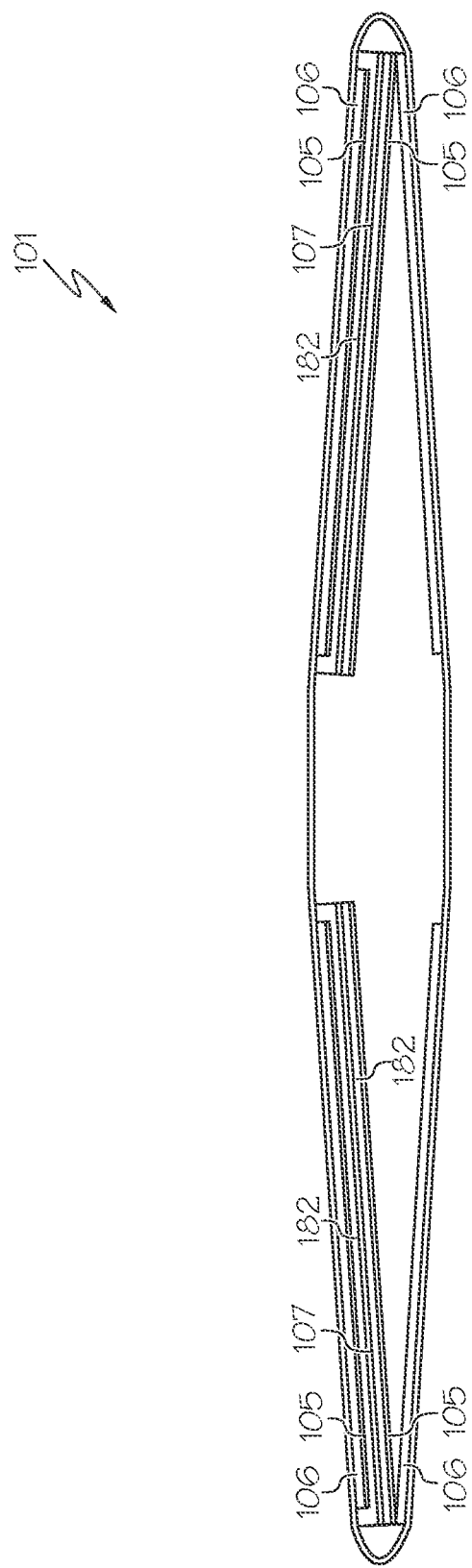
FIG. 1A schematically depicts a cross section view of an artificial muscle with titanium dioxide ($TiO_2$) nanomaterial composite electrical insulating layered tape structures affixed to aluminum film electrodes, according to one or more embodiments shown and described herein.

Embodiments described herein are directed to artificial muscles configured to exert outward pressure. The artificial muscles are more lightweight than traditional motors or actuators, making them better-suited for any potential use that could benefit from a lighter and stronger actuator. The artificial muscles described herein may include a housing having an electrode region and an expandable fluid region, a first electrode and a second electrode each disposed in the electrode region of the housing. Composite electrical insulating layered structures in contact with the electrodes includes titanium dioxide ($TiO_2$) (as a discrete layer, a region of nanoparticles, or a combination thereof) surrounded by adhesive surfaces, which may be surrounded by flexible electrical insulators, such as a biaxially oriented polypropylene (BOPP) film. A dielectric fluid (i.e., a dielectric liquid or dielectric gas) may be disposed within the housing, where the first and second electrodes may electrostatically attract, inflating the expandable fluid region with dielectric fluid and thereby applying outward pressure. The artificial muscle may then be utilized to provide a variety of beneficial types of pressure, such as massaging patterns of pressure, haptic feedback based upon a user, and/or as output from an infotainment device, in which the amount of pressure may vary depending on the thickness and/or amount of $TiO_2$ present within the composite electrical insulating layered structures. Various embodiments of artificial muscles and the operation of which, are described in more detail herein. Whenever possible, the same reference numerals will be used throughout the drawings to refer to the same or like parts.

Referring now to FIG. 1A, an artificial muscle 101 may reside within a vehicle (car, truck, sport utility vehicle, van, motorcycle, aircraft, boat, ship, submersible craft, spacecraft, and the like), a house, an office, wearables (clothing, hats, shoes), furniture (seat cushion, arm rest, a foot rest, any other portion which may have contact with a user), and the like. An artificial muscle 101 may actuate/de-actuate at varying rates, intervals, intensity, and the like over time. In this way, any type of pressure pattern can be applied, such as changing pressure, which may be utilized for massaging pressure such as in the form of waves of pressure over time.

The artificial muscle 101 is schematically depicted as having a pair of electrodes 106 each in contact with (such as via an adhesive, fastener, or the like) a flexible electrical insulator 105 such as BOPP film or any other suitable type of electrical insulator. In this embodiment, the BOPP film may be wrapped around adhesive surfaces 182 (such as an acrylic adhesive and/or any other suitable adhesive). Between the adhesive surfaces 182 resides an electrical insulator layer 107, which in this embodiment may be a composite of nanomaterials such as $TiO_2$ nanoparticles doped (e.g., covered with, immersed in, and the like) with 1% manganese, although any suitable concentration of manganese and/or any other suitable substance may be utilized for the nanoparticles and/or doping of the nanoparticles.

The electrical insulator layer 107 (i.e., a layer of $TiO_2$ in this embodiment) may have a thickness in the range of 10-15 μm (micrometer), although any suitable thickness may be utilized in other embodiments. In another embodiment, the thickness of the $TiO_2$ layer may be in a range that exceeds 0.1 μm and is less than 100 μm. As shown with respect to FIG. 1B, the thickness of the $TiO_2$ layer may impact artificial muscle force output, with a goal of increasing permittivity (dielectric constant) between the electrodes 106. Permittivity is the ability of a material to store electrical potential energy under the influence of an electric field, and is measured by the ratio of the capacitance of a capacitor with the material as dielectric to its capacitance with vacuum as dielectric. Rather than a constant, $TiO_2$ may have differing dielectric values in relation to $TiO_2$ particle size (which can vary) in relation to the $TiO_2$ surface area. In determining an amount of thickness for the electrical insulator layer 107, it may be desirable to increase the thickness of the $TiO_2$ layer such that a value of the increased thickness, squared, is less than the corresponding increase in the dielectric constant.

Figure 1B:
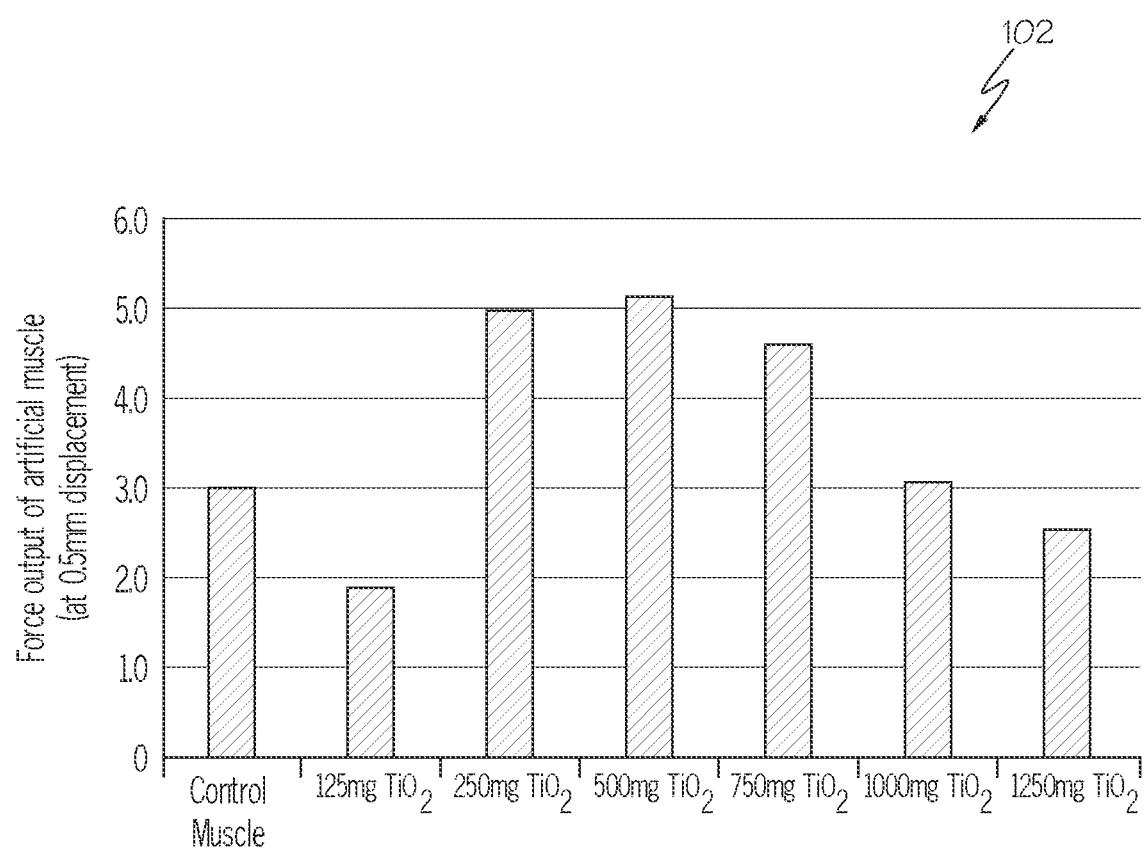
FIG. 1B depicts a comparison chart of artificial muscle force output improvement for the artificial muscle realized from using $TiO_2$ nanoparticle composite electrical insulators, according to one or more embodiments shown and described herein.

Referring now to FIG. 1B, a graph 102 depicts artificial muscle force output improvement for an artificial muscle as realized from using $TiO_2$ nanoparticle composite electrical insulators. Specifically, the graph 102 depicts the output force at 0.5 mm displacement for a series of oval-shaped artificial muscles using a 7 kV actuation voltage. The vertical axis represents an increasing amount of force output by an artificial muscle as measured in millimeters (i.e., the amount of displacement provided by an artificial muscle). The horizontal axis represents an increasing amount of $TiO_2$ as indicated by the mass of $TiO_2$ nanoparticles per 10 mL of methanol slurry used in fabrication of the nanoparticle composite electrical insulator for each respective muscle. When a $TiO_2$ thin film is introduced between adhesive surface layers (such as insulation tape) to make a nanomaterial composite layered structure, in this embodiment the force output of the artificial muscle may be increased (by way of non-limiting example) by 72% over a control muscle does not utilize any $TiO_2$ layer or nanoparticles.

Figure 2A:
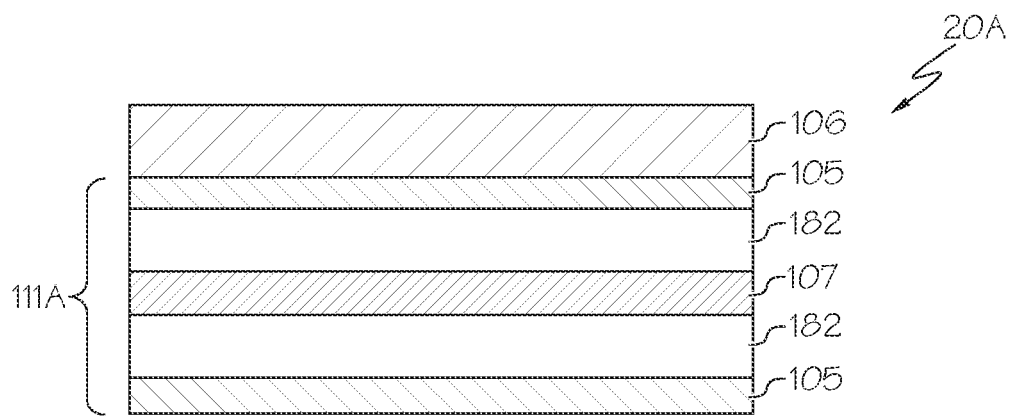
FIG. 2A schematically depicts a cross section view of an embodiment of an electrode having a $TiO_2$ nanomaterial composite electrical insulating layered tape structure having a discrete $TiO_2$ nanoparticle layer, according to one or more embodiments shown and described herein.

Referring now to FIG. 2A, an embodiment depicts an electrode 106 in contact with a composite electrical insulating layered structure 111. A having a discrete electrical insulator layer 107. Within the composite electrical insulating layered structure 111A, the electrical insulator layer 107 resides between adhesive surfaces 182. The adhesive surfaces 182 are located between the electrical insulator layer 107 and respective flexible electrical insulators 105, one of which is in direct contact with the electrode 106.

Figure 2B:
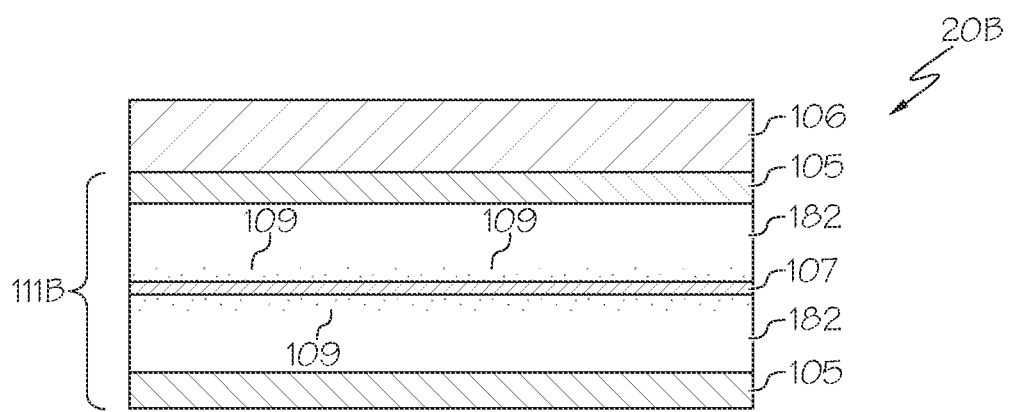
FIG. 2B schematically depicts a cross section view of another embodiment of an electrode having a $TiO_2$ nanomaterial composite electrical insulating layered tape structure having a $TiO_2$ nanoparticle layer partially mixed into surrounding adhesive layers, according to one or more embodiments shown and described herein.

Referring to FIG. 2B, another embodiment depicts an electrode 106 in contact with a composite electrical insulating layered structure 111B having a discrete electrical insulator layer 107 thinner than the electrical insulator layer 107 illustrated in FIG. 2A, along with electrical insulator nanoparticles 109 residing within the adhesive surfaces 182 proximate to the discrete electrical insulator layer 107. In some embodiments, this may be due to electrical insulator nanoparticles 109 (e.g., $TiO_2$ nanoparticles) from the electrical insulator layer 107 becoming pushed into adjacent portions of the adhesive surfaces 182 due to time, pressure, friction, and/or the like. In this embodiment, the electrical insulator nanoparticles 109 may reside within areas of the adhesive surfaces 182 adjacent the remaining electrical insulator layer 107 that generally correspond to the electrical insulator layer 107 depicted in FIG. 2A. In other embodiments, the electrical insulator nanoparticles 109 may be distributed into other areas of the adhesive surfaces 182 beyond this. In some embodiments, the electrical insulator nanoparticles 109 may be in a concentration/density that increases with proximity to the electrical insulator layer. The adhesive surfaces 182 are located between the electrical insulator layer 107 and respective flexible electrical insulators 105, one of which is in direct contact with the electrode 106.

Figure 2C:
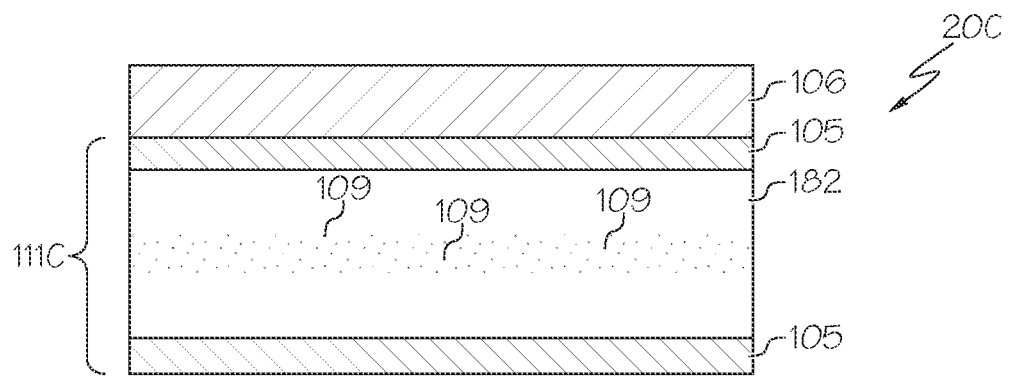
FIG. 2C schematically depicts a cross section view of another embodiment of an electrode having a $TiO_2$ nanomaterial composite electrical insulating layered tape structure having $TiO_2$ nanoparticles mixed within a combined adhesive layer, according to one or more embodiments shown and described herein.

Referring to FIG. 2C, a further embodiment depicts an electrode 106 in contact with a composite electrical insulating layered structure 111C having electrical insulator nanoparticles 109 disposed within an adhesive surface 182 but without a discreet electrical insulator layer. For example, the adhesives may join over time to form a single adhesive surface 182. In another embodiment, there may be two or more adhesive surfaces 182. In this embodiment, the electrical insulator nanoparticles 109 may reside in areas adjacent the remaining electrical insulator layer 107 that generally correspond to the electrical insulator layer 107 depicted in FIG. 2A. In other embodiments, the electrical insulator nanoparticles 109 may be distributed into other areas of the adhesive surfaces 182 beyond this. In some embodiments, the electrical insulator nanoparticles 109 may be in a concentration/density higher in the area corresponding to the electrical insulator layer 107 with the one or more adhesive surfaces 182, and which may decrease in concentration/density further out. This may be due, for example, to the electrical insulator layer 107 in FIGS. 2A-2B having been completely dissolved within the adhesive surface(s) 182. The adhesive surface(s) 182 is/are located between the electrical insulator layer 107 and respective flexible electrical insulators 105, one of which is in direct contact with the electrode 106.

Figure 3:
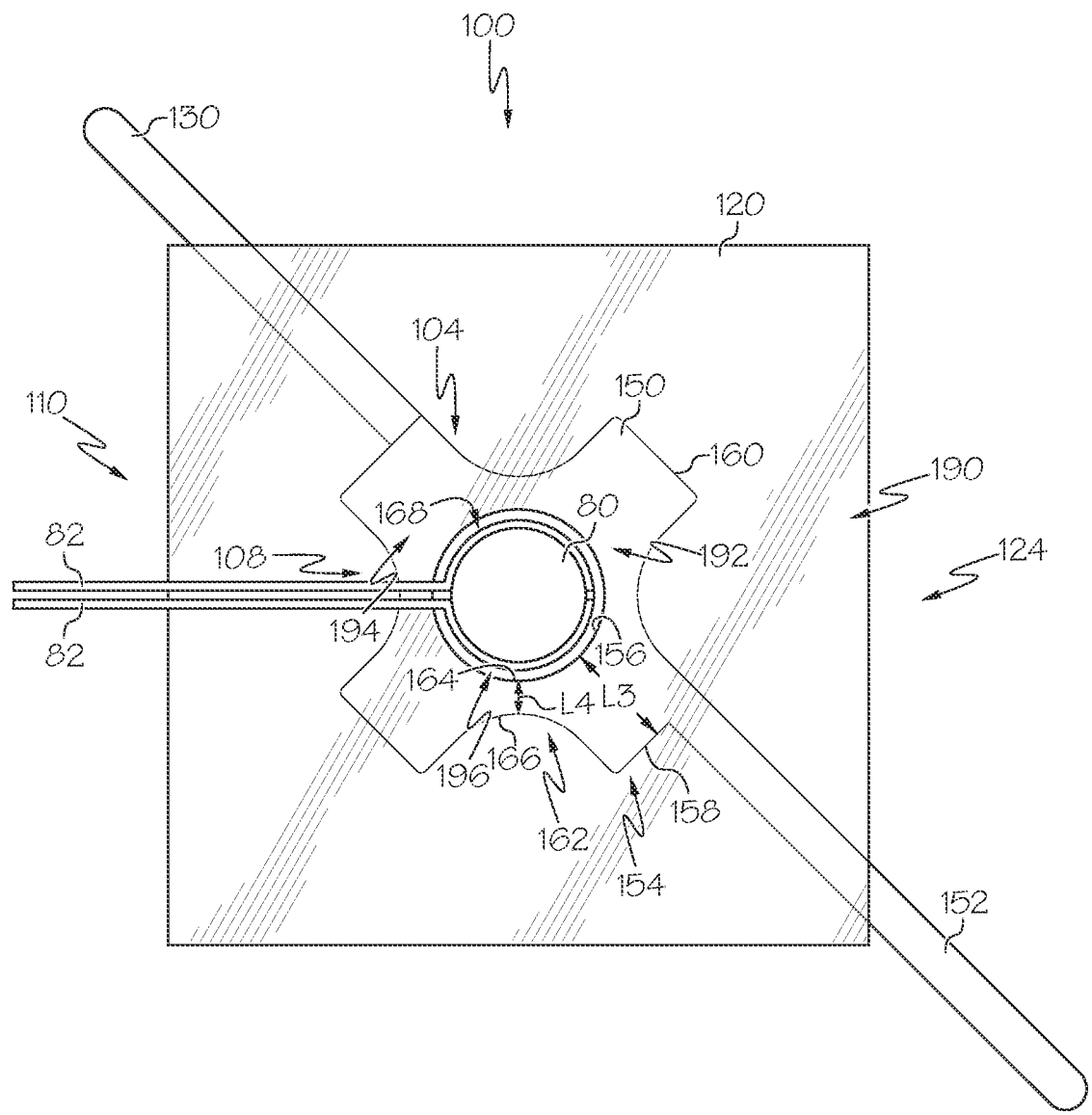
FIG. 3 schematically depicts a top view of an illustrative artificial muscle of the artificial muscle of FIG. 1 with a pressure sensor affixed thereon, according to one or more embodiments shown and described herein.
Figure 4:
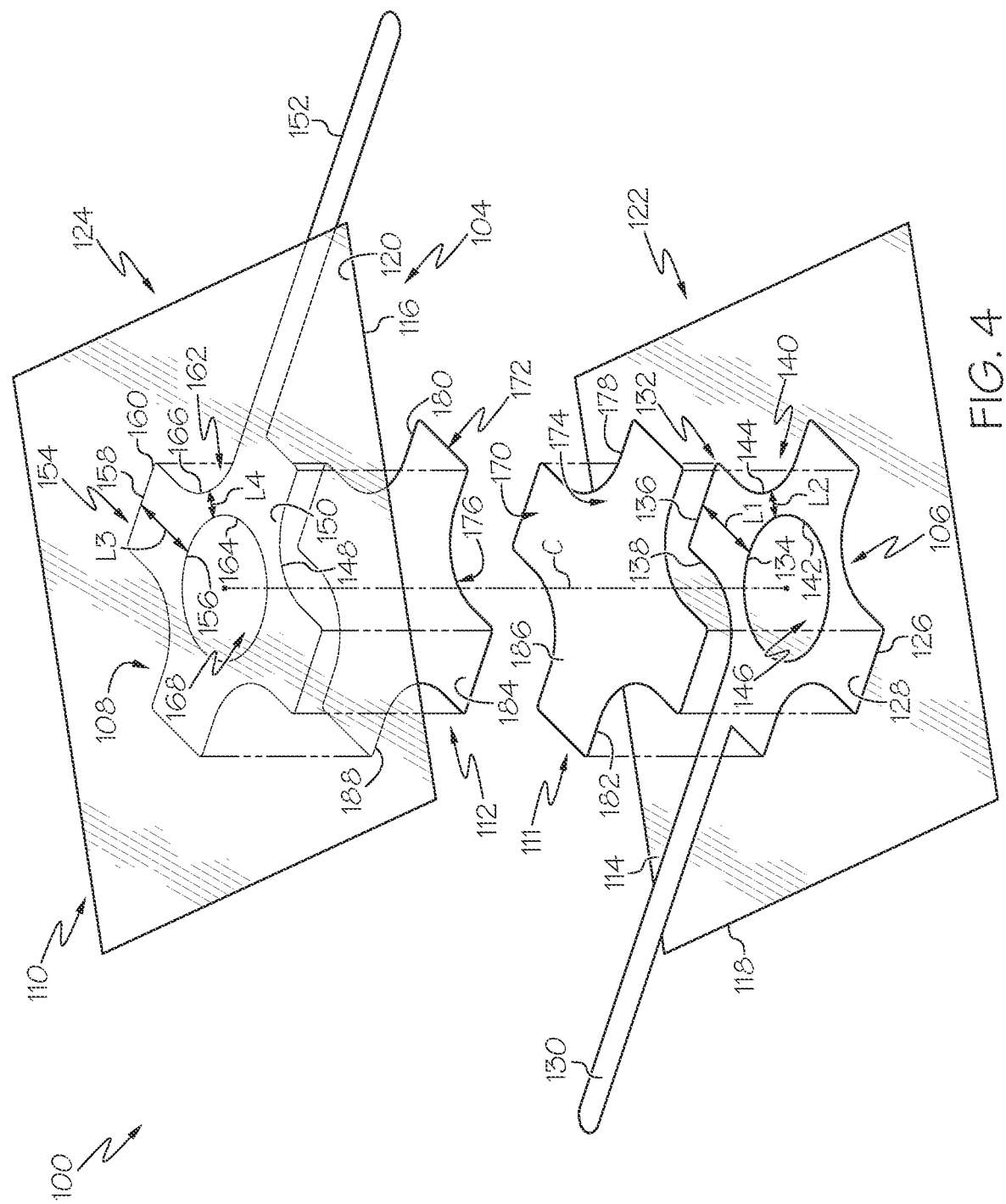
FIG. 4 schematically depicts an exploded view of the artificial muscle of FIG. 3 without the pressure sensor affixed thereon, according to one or more embodiments shown and described herein.
Figure 5:
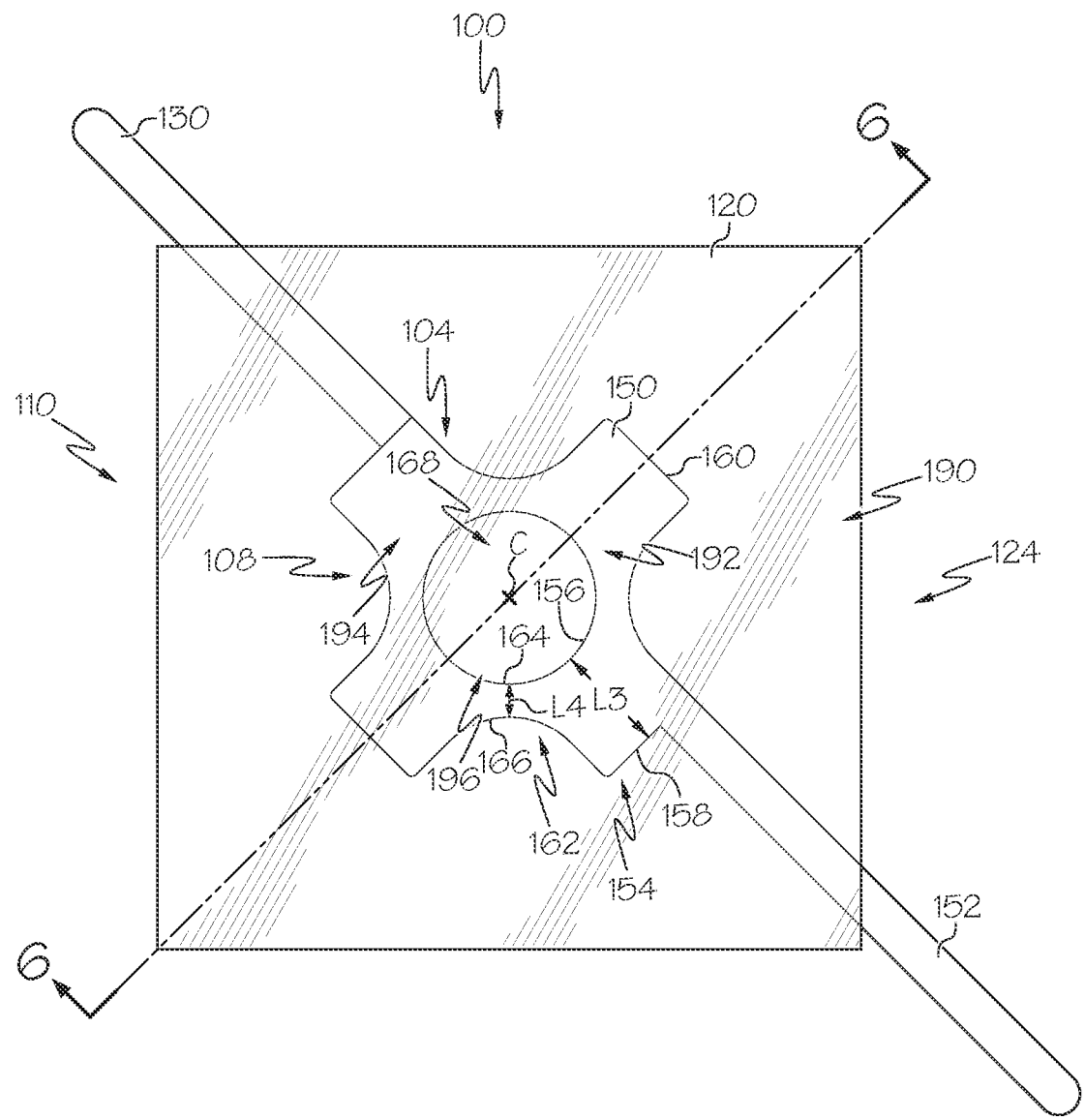
FIG. 5 schematically depicts a top view of the artificial muscle of FIG. 4, according to one or more embodiments shown and described herein.

Referring now to FIGS. 3-5, an artificial muscle 100 is depicted in more detail, and may also include an electrode pair 104 disposed in a housing 110 together with a dielectric fluid 198. The electrode pair 104 is disposed in an electrode region 194 of the housing 110, adjacent an expandable fluid region 196. In operation, voltage may be applied to the electrode pair 104, drawing the electrode pair 104 together, which directs dielectric fluid into the expandable fluid region 196, expanding the expandable fluid region 196. Actuation of artificial muscles 10 may be made to maintain a periodic actuation pressure. In operation, actuation of the one or more artificial muscles 100 may be controlled by an actuation system 1300, described in more detail with respect to FIG. 13. This may include, for example, utilizing a pressure value (Pa/pascal, PSI, etc.) to determine the actuation amount of the one or more artificial muscles 100.

The artificial muscle 100 includes the housing 110, the electrode pair 104, including a first electrode 106 and a second electrode 108, fixed to opposite surfaces of the housing 110, a first composite electrical insulating layered structure 11 IC fixed to the first electrode 106, and a second composite electrical insulating layered structure 112 fixed to the second electrode 108. In some embodiments, the housing 110 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 110 are heat-sealable. In other embodiments, the housing 110 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

While the embodiments described herein primarily refer to the housing 110 as comprising the first film layer 122 and the second film layer 124, as opposed to the one-piece housing, it should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene.

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 100 is negatively charged.

The first electrode 106 has a film-facing surface 126 and an opposite inner surface 128. The first electrode 106 is positioned against the first film layer 122, specifically, the first inner surface 114 of the first film layer 122. In addition, the first electrode 106 includes a first terminal 130 extending from the first electrode 106 past an edge of the first film layer 122 such that the first terminal 130 can be connected to a power supply to actuate the first electrode 106. Specifically, the terminal is coupled, either directly or in series, to a power supply and a controller of an actuation system 1300, as shown in FIG. 13. Similarly, the second electrode 108 has a film-facing surface 148 and an opposite inner surface 150. The second electrode 108 is positioned against the second film layer 124, specifically, the second inner surface 116 of the second film layer 124. The second electrode 108 includes a second terminal 152 extending from the second electrode 108 past an edge of the second film layer 124 such that the second terminal 152 can be connected to a power supply and a controller of the actuation system 1300 to actuate the second electrode 108.

The first electrode 106 includes two or more tab portions 132 and two or more bridge portions 140. Each bridge portion 140 is positioned between adjacent tab portions 132, interconnecting these adjacent tab portions 132. Each tab portion 132 has a first end 134 extending radially from a center axis C of the first electrode 106 to an opposite second end 136 of the tab portion 132, where the second end 136 defines a portion of an outer perimeter 138 of the first electrode 106. Each bridge portion 140 has a first end 142 extending radially from the center axis C of the first electrode 106 to an opposite second end 144 of the bridge portion 140 defining another portion of the outer perimeter 138 of the first electrode 106. Each tab portion 132 has a tab length L1 and each bridge portion 140 has a bridge length L2 extending in a radial direction from the center axis C of the first electrode 106. The tab length L1 is a distance from the first end 134 to the second end 136 of the tab portion 132 and the bridge length L2 is a distance from the first end 142 to the second end 144 of the bridge portion 140. The tab length L1 of each tab portion 132 is longer than the bridge length L2 of each bridge portion 140. In some embodiments, the bridge length L2 is 20% to 50% of the tab length L1, such as 30% to 40% of the tab length L1.

Figure 6:
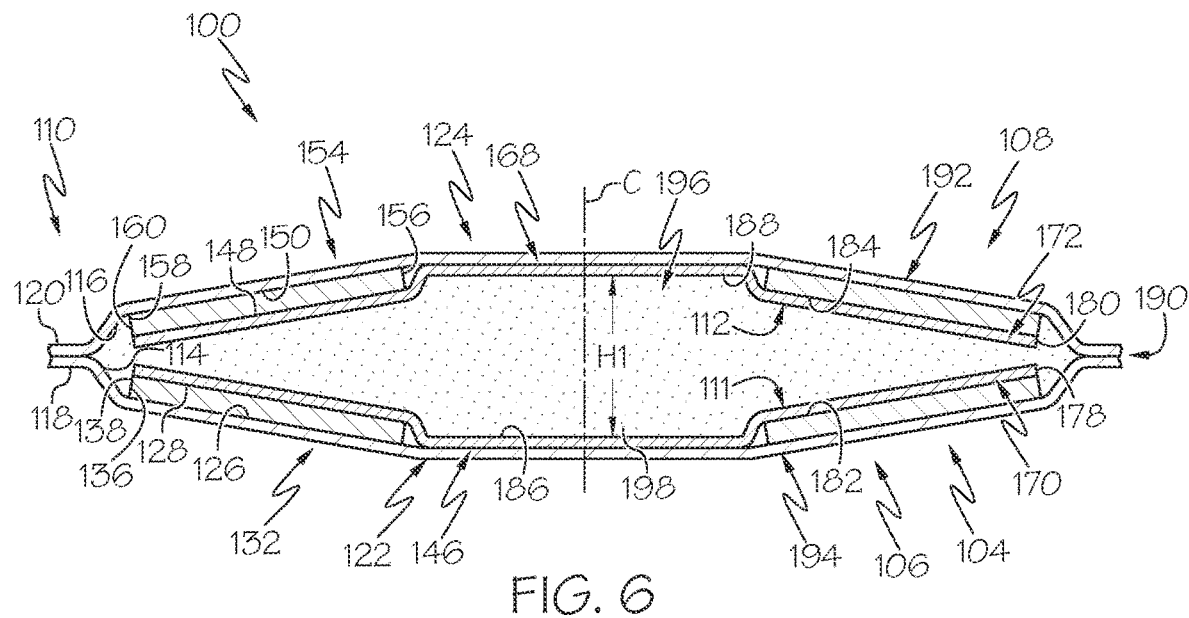
FIG. 6 schematically depicts a cross-sectional view of the artificial muscle of FIG. 4 taken along line 6-6 in FIG. 5 in a non-actuated state, according to one or more embodiments shown and described herein.

In some embodiments, the two or more tab portions 132 are arranged in one or more pairs of tab portions 132. Each pair of tab portions 132 includes two tab portions 132 arranged diametrically opposed to one another. In some embodiments, the first electrode 106 may include only two tab portions 132 positioned on opposite sides or ends of the first electrode 106. In some embodiments, as shown in FIGS. 4-6, the first electrode 106 includes four tab portions 132 and four bridge portions 140 interconnecting adjacent tab portions 132. In this embodiment, the four tab portion 132 are arranged as two pairs of tab portions 132 diametrically opposed to one another. Furthermore, as shown, the first terminal 130 extends from the second end 136 of one of the tab portions 132 and is integrally formed therewith.

Like the first electrode 106, the second electrode 108 includes at least a pair of tab portions 154 and two or more bridge portions 162. Each bridge portion 162 is positioned between adjacent tab portions 154, interconnecting these adjacent tab portions 154. Each tab portion 154 has a first end 156 extending radially from a center axis C of the second electrode 108 to an opposite second end 158 of the tab portion 154, where the second end 158 defines a portion of an outer perimeter 160 of the second electrode 108. Due to the first electrode 106 and the second electrode 108 being coaxial with one another, the center axis C of the first electrode 106 and the second electrode 108 are the same. Each bridge portion 162 has a first end 164 extending radially from the center axis C of the second electrode to an opposite second end 166 of the bridge portion 162 defining another portion of the outer perimeter 160 of the second electrode 108. Each tab portion 154 has a tab length L3 and each bridge portion 162 has a bridge length L4 extending in a radial direction from the center axis C of the second electrode 108. The tab length L3 is a distance from the first end 156 to the second end 158 of the tab portion 154 and the bridge length L4 is a distance from the first end 164 to the second end 166 of the bridge portion 162. The tab length L3 is longer than the bridge length L4 of each bridge portion 162. In some embodiments, the bridge length L4 is 20% to 50% of the tab length L3, such as 30% to 40% of the tab length L3.

In some embodiments, the two or more tab portions 154 are arranged in one or more pairs of tab portions 154. Each pair of tab portions 154 includes two tab portions 154 arranged diametrically opposed to one another. In some embodiments, the second electrode 108 may include only two tab portions 154 positioned on opposite sides or ends of the first electrode 106. In some embodiments, as shown in FIGS. 4-6, the second electrode 108 includes four tab portions 154 and four bridge portions 162 interconnecting adjacent tab portions 154. In this embodiment, the four tab portions 154 are arranged as two pairs of tab portions 154 diametrically opposed to one another. Furthermore, as shown, the second terminal 152 extends from the second end 158 of one of the tab portions 154 and is integrally formed therewith.

Figure 7:
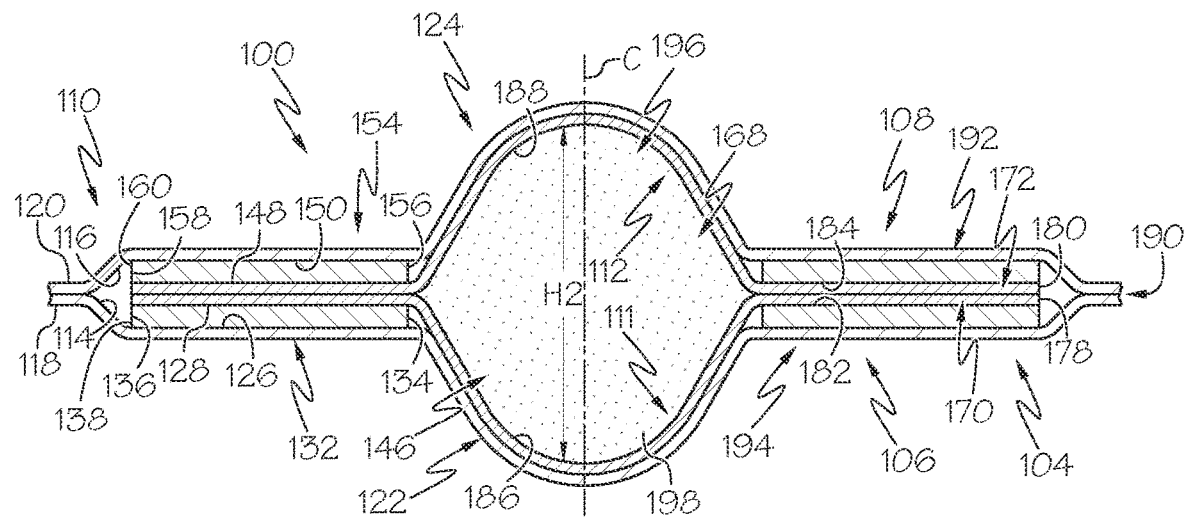
FIG. 7 schematically depicts a cross-sectional view of the artificial muscle of FIG. 4 taken along line 6-6 in FIG. 5 in an actuated state, according to one or more embodiments shown and described herein.
Figure 8:
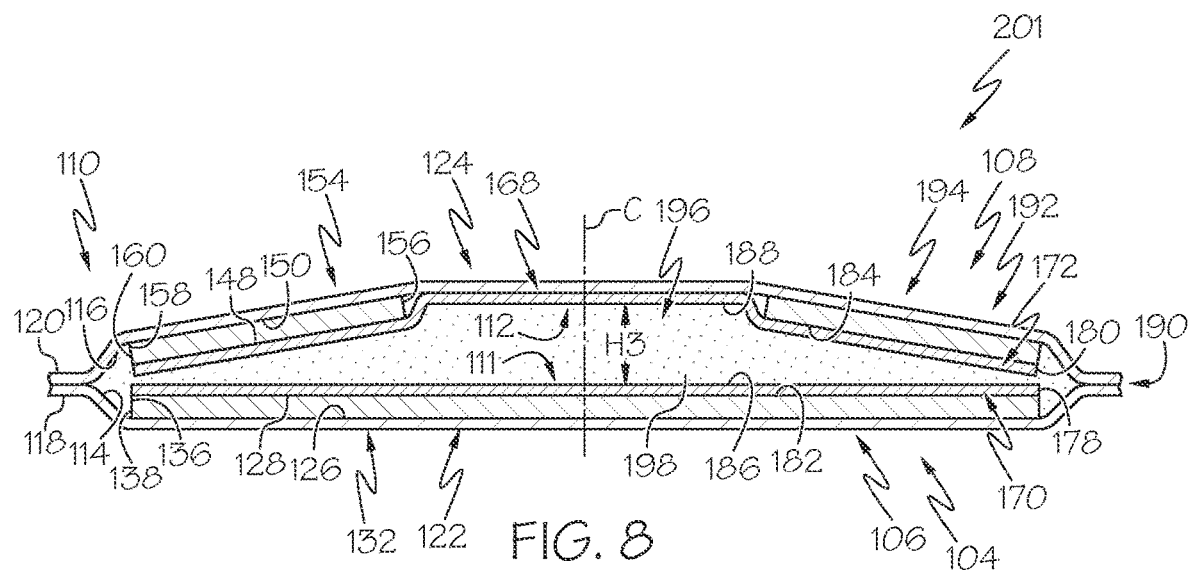
FIG. 8 schematically depicts a cross-sectional view of another illustrative artificial muscle in a non-actuated state, according to one or more embodiments shown and described herein.
Figure 9:
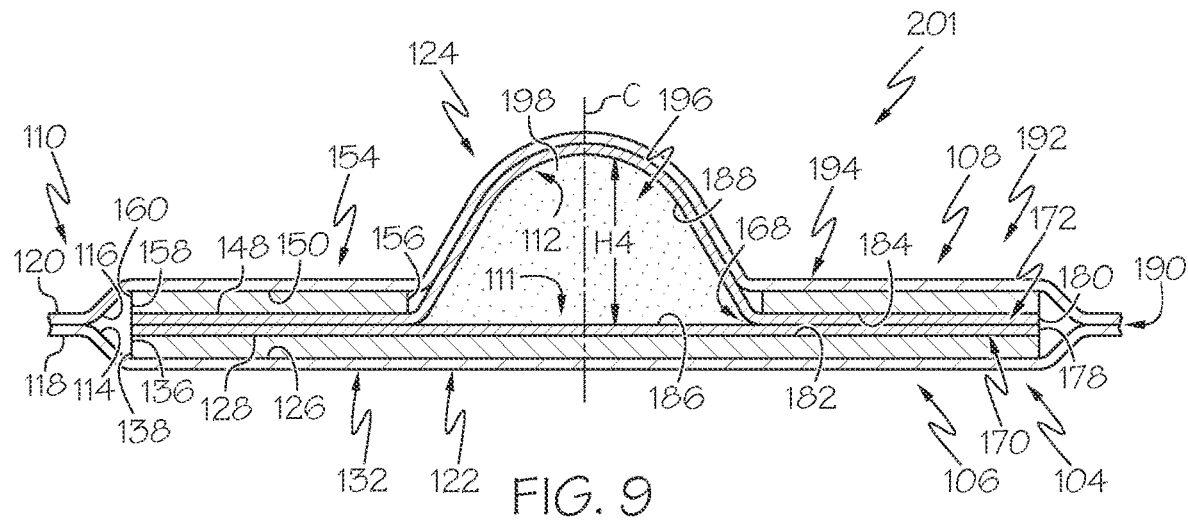
FIG. 9 schematically depicts a cross-sectional view of the artificial muscle of FIG. 4 in an actuated state, according to one or more embodiments shown and described herein.

Referring now to FIGS. 3-9, at least one of the first electrode 106 and the second electrode 108 has a central opening formed therein between the first end 134 of the tab portions 132 and the first end 142 of the bridge portions 140. In FIGS. 6 and 7, the first electrode 106 has a central opening 146. However, it should be understood that the first electrode 106 does not need to include the central opening 146 when a central opening is provided within the second electrode 108, as shown in FIGS. 8 and 9. Alternatively, the second electrode 108 does not need to include the central opening when the central opening 146 is provided within the first electrode 106. Referring to FIGS. 3-9, the first composite electrical insulating layered structure 111 and the second composite electrical insulating layered structure 112 have a geometry generally corresponding to the first electrode 106 and the second electrode 108, respectively. Thus, the first composite electrical insulating layered structure 111 and the second composite electrical insulating layered structure 112 each have tab portions 170, 172 and bridge portions 174, 176 corresponding to like portions on the first electrode 106 and the second electrode 108. Further, the composite electrical insulating layered structure 111 and the second composite electrical insulating layered structure 112 each have an outer perimeter 178, 180 corresponding to the outer perimeter 138 of the first electrode 106 and the outer perimeter 160 of the second electrode 108, respectively, when positioned thereon.

It should be appreciated that, in some embodiments, the first composite electrical insulating layered structure 111 and the second composite electrical insulating layered structure 112 generally include the same structure and composition. As such, in some embodiments, the first composite electrical insulating layered structure 111 and the second composite electrical insulating layered structure 112 each include an adhesive surface 182, 184 and an opposite non-sealable surface 186, 188, respectively. Thus, in some embodiments, the first composite electrical insulating layered structure 111 and the second composite electrical insulating layered structure 112 are each a polymer tape adhered to the inner surface 128 of the first electrode 106 and the inner surface 150 of the second electrode 108, respectively.

Referring again to FIGS. 3-9, the artificial muscle 100 is shown in its assembled form with the first terminal 130 of the first electrode 106 and the second terminal 152 of the second electrode 108 extending past an outer perimeter of the housing 110, i.e., the first film layer 122 and the second film layer 124. As shown in FIG. 4, the second electrode 108 is stacked on top of the first electrode 106 and, therefore, the first electrode 106, the first film layer 122, and the second film layer 124 are not shown. In its assembled form, the first electrode 106, the second electrode 108, the first composite electrical insulating layered structure 111, and the second composite electrical insulating layered structure 112 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, or the like.

The first electrode 106, the second electrode 108, the first composite electrical insulating layered structure 111, and the second composite electrical insulating layered structure 112 provide a barrier that prevents the first film layer 122 from sealing to the second film layer 124 forming an unsealed portion 192. The unsealed portion 192 of the housing 110 includes the electrode region 194, in which the electrode pair 104 is provided, and the expandable fluid region 196, which is surrounded by the electrode region 194. The central openings 146, 168 of the first electrode 106 and the second electrode 108 form the expandable fluid region 196 and are arranged to be axially stacked on one another. Although not shown, the housing 110 may be cut to conform to the geometry of the electrode pair 104 and reduce the size of the artificial muscle 100, namely, the size of the sealed portion 190.

A dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 100 using a needle or other suitable injection device.

Referring now to FIGS. 6 and 7, the artificial muscle 100 is actuatable between a non-actuated state and an actuated state. In the non-actuated state, the first electrode 106 and the second electrode 108 are partially spaced apart from one another proximate the central openings 146, 168 thereof and the first end 134, 156 of the tab portions 132, 154. The second end 136, 158 of the tab portions 132, 154 remain in position relative to one another due to the housing 110 being sealed at the outer perimeter 138 of the first electrode 106 and the outer perimeter 160 of the second electrode 108. In the actuated state, as shown in FIG. 7, the first electrode 106 and the second electrode 108 are brought into contact with and oriented parallel to one another to force the dielectric fluid 198 into the expandable fluid region 196. This causes the dielectric fluid 198 to flow through the central openings 146, 168 of the first electrode 106 and the second electrode 108 and inflate the expandable fluid region 196.

Referring now to FIG. 6, the artificial muscle 100 is shown in the non-actuated state. The electrode pair 104 is provided within the electrode region 194 of the unsealed portion 192 of the housing 110. The central opening 146 of the first electrode 106 and the central opening 168 of the second electrode 108 are coaxially aligned within the expandable fluid region 196. In the non-actuated state, the first electrode 106 and the second electrode 108 are partially spaced apart from and non-parallel to one another. Due to the first film layer 122 being sealed to the second film layer 124 around the electrode pair 104, the second end 136, 158 of the tab portions 132, 154 are brought into contact with one another. Thus, dielectric fluid 198 is provided between the first electrode 106 and the second electrode 108, thereby separating the first end 134, 156 of the tab portions 132, 154 proximate the expandable fluid region 196. Stated another way, a distance between the first end 134 of the tab portion 132 of the first electrode 106 and the first end 156 of the tab portion 154 of the second electrode 108 is greater than a distance between the second end 136 of the tab portion 132 of the first electrode 106 and the second end 158 of the tab portion 154 of the second electrode 108. This results in the electrode pair 104 zippering toward the expandable fluid region 196 when actuated. In some embodiments, the first electrode 106 and the second electrode 108 may be flexible. Thus, as shown in FIG. 5, the first electrode 106 and the second electrode 108 are convex such that the second ends 136, 158 of the tab portions 132, 154 thereof may remain close to one another, but spaced apart from one another proximate the central openings 146, 168. In the non-actuated state, the expandable fluid region 196 has a first height H1.

When actuated, as shown in FIG. 7, the first electrode 106 and the second electrode 108 zipper toward one another from the second ends 144, 158 of the tab portions 132, 154 thereof, thereby pushing the dielectric fluid 198 into the expandable fluid region 196. As shown, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

In order to move the first electrode 106 and the second electrode 108 toward one another, a voltage is applied by a power supply (such as power supply 48 of FIG. 13). In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 and the first composite electrical insulating layered structure 111 to deform in a first axial direction along the center axis C of the first electrode 106 and causes the second film layer 124 and the second electrical composite electrical insulating layered structure 112 to deform in an opposite second axial direction along the center axis C of the second electrode 108. Once the voltage being supplied to the first electrode 106 and the second electrode 108 is discontinued, the first electrode 106 and the second electrode 108 return to their initial, non-parallel position in the non-actuated state.

It should be appreciated that the present embodiments of the artificial muscle 100 disclosed herein, specifically, the tab portions 132, 154 with the interconnecting bridge portions 174, 176, provide a number of improvements over actuators that do not include the tab portions 132, 154, such as hydraulically amplified self-healing electrostatic (HA-SEL) actuators described in the paper titled "*Hydraulically amplified self-healing electrostatic actuators with muscle-like performance*" by E. Acome. S. K. Mitchell, T. G. Morrissey, M. B. Emmett, C. Benjamin, M. King, M. Radakovitz, and C. Keplinger (Science 5 Jan. 2018: Vol. 359, Issue 6371, pp. 61-65). Embodiments of the artificial muscle 100 including two pairs of tab portions 132, 154 on each of the first electrode 106 and the second electrode 108, respectively, reduces the overall mass and thickness of the artificial muscle 100, reduces the amount of voltage required during actuation, and decreases the total volume of the artificial muscle 100 without reducing the amount of resulting force after actuation as compared to known HASEL actuators including donut-shaped electrodes having a uniform, radially-extending width. More particularly, the tab portions 132, 154 of the artificial muscle 100 provide zipping fronts that result in increased actuation power by providing localized and uniform hydraulic actuation of the artificial muscle 100 compared to HASEL actuators including donut-shaped electrodes. Specifically, one pair of tab portions 132, 154 provides twice the amount of actuator power per unit volume as compared to donut-shaped HASEL actuators, while two pairs of tab portions 132, 154 provide four times the amount of actuator power per unit volume. The bridge portions 174, 176 interconnecting the tab portions 132, 154 also limit buckling of the tab portions 132, 154 by maintaining the distance between adjacent tab portions 132, 154 during actuation. Because the bridge portions 174, 176 are integrally formed with the tab portions 132, 154, the bridge portions 174, 176 also prevent leakage between the tab portions 132, 154 by eliminating attachment locations that provide an increased risk of rupturing.

In operation, when the artificial muscle 100 is actuated by providing a voltage and applying the voltage to the electrode pair 104 of the artificial muscle 100, expansion of the expandable fluid region 196 produces a force of 3 Newton-millimeters (N·mm) per cubic centimeter ($cm^3$) of actuator volume or greater, such as 4 N·mm per $cm^3$ or greater, 5 N·mm per $cm^3$ or greater, 6 N·mm per $cm^3$ or greater, 7 N·mm per $cm^3$ or greater, 8 N·mm per $cm^3$ or greater, or the like. Providing the voltage may comprise generating the voltage, for example, in an embodiment in which the power supply 48 (FIG. 13) is a battery, converting the voltage, for example in embodiment in which the power supply 48 (FIG. 13) is a power adaptor, or any other known or yet to be developed technique for readying a voltage for application. In one example, when the artificial muscle 100 is actuated by a voltage of 9.5 kilovolts (kV), the artificial muscle 100 provides a resulting force of 5 N. In another example, when the artificial muscle 100 is actuated by a voltage of 10 kV the artificial muscle 100 provides 440% strain under a 500 gram load.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146, 168 in the first electrode 106 and the second electrode 108. Thus, the degree of displacement within the expandable fluid region 196 may alternatively, or in addition, be controlled by increasing or reducing the size of the central openings 146, 168.

As shown in FIGS. 8 and 9, another embodiment of an artificial muscle 201 is illustrated. The artificial muscle 201 is substantially similar to the artificial muscle 100. As such, like structure is indicated with like reference numerals. However, as shown, the first electrode 106 does not include a central opening. Thus, only the second electrode 108 includes the central opening 168 formed therein. As shown in FIG. 8, the artificial muscle 201 is in the non-actuated state with the first electrode 106 being planar and the second electrode 108 being convex relative to the first electrode 106. In the non-actuated state, the expandable fluid region 196 has a first height H3. In the actuated state, as shown in FIG. 9, the expandable fluid region 196 has a second height H4, which is greater than the first height H3. It should be appreciated that by providing the central opening 168 only in the second electrode 108 as opposed to both the first electrode 106 and the second electrode 108, the total deformation may be formed on one side of the artificial muscle 201. In addition, because the total deformation is formed on only one side of the artificial muscle 201, the second height H4 of the expandable fluid region 196 of the artificial muscle 201 extends further from a longitudinal axis perpendicular to the central axis C of the artificial muscle 201 than the second height H2 of the expandable fluid region 196 of the artificial muscle 100 when all other dimensions, orientations, and volume of dielectric fluid are the same.

In some embodiments, as shown in FIG. 3, a pressure sensor 80 may reside on the housing 110 and be aligned with the central opening 168 or central opening 146, which are openings in the first electrode 106 and second electrode 108, respectively. In some embodiments, the pressure sensor 80 may be disposed on the expandable fluid region 196 of the housing 110. In other embodiments, the pressure sensor 80 may be located on any suitable surface of the housing 110 or an artificial muscle 100.

In some embodiments, different pressure sensors 80 may be located at different locations with respect to different embodiments of housings 110 and/or artificial muscles 100. In this embodiment, the pressure sensor 80 has two sensor protrusions 82 that extend outwardly from the pressure sensor 80 and may be disposed between the inner layer 30 and outer layer 20. Sensor protrusions may be used, for example, to wirelessly communicate with other components, such as a controller 50 (as shown in FIG. 13) and/or other wireless sensors located on other artificial muscles 100. In other embodiments, any number of sensor protrusions 82 of any shape, size, and/or configuration may be utilized. In still other embodiments, the pressure sensor 80 may have no sensor protrusions 82.

In some embodiments, the pressure sensor 80 may be of any suitable type, such as, by way of non-limiting example, absolute, gauge, or differential pressure sensors. Sensing by the pressure sensor 80 may include any suitable technique such as resistive sensing, capacitive sensing, piezoelectric sensing, optical sensing, micro electro-mechanical system (MEMS), or any other suitable type of pressure sensing technique. Output from the pressure sensor 80 may be by millivolt-output transducers, volt-output transducers, transmitters, or any other suitable components.

Figure 10:
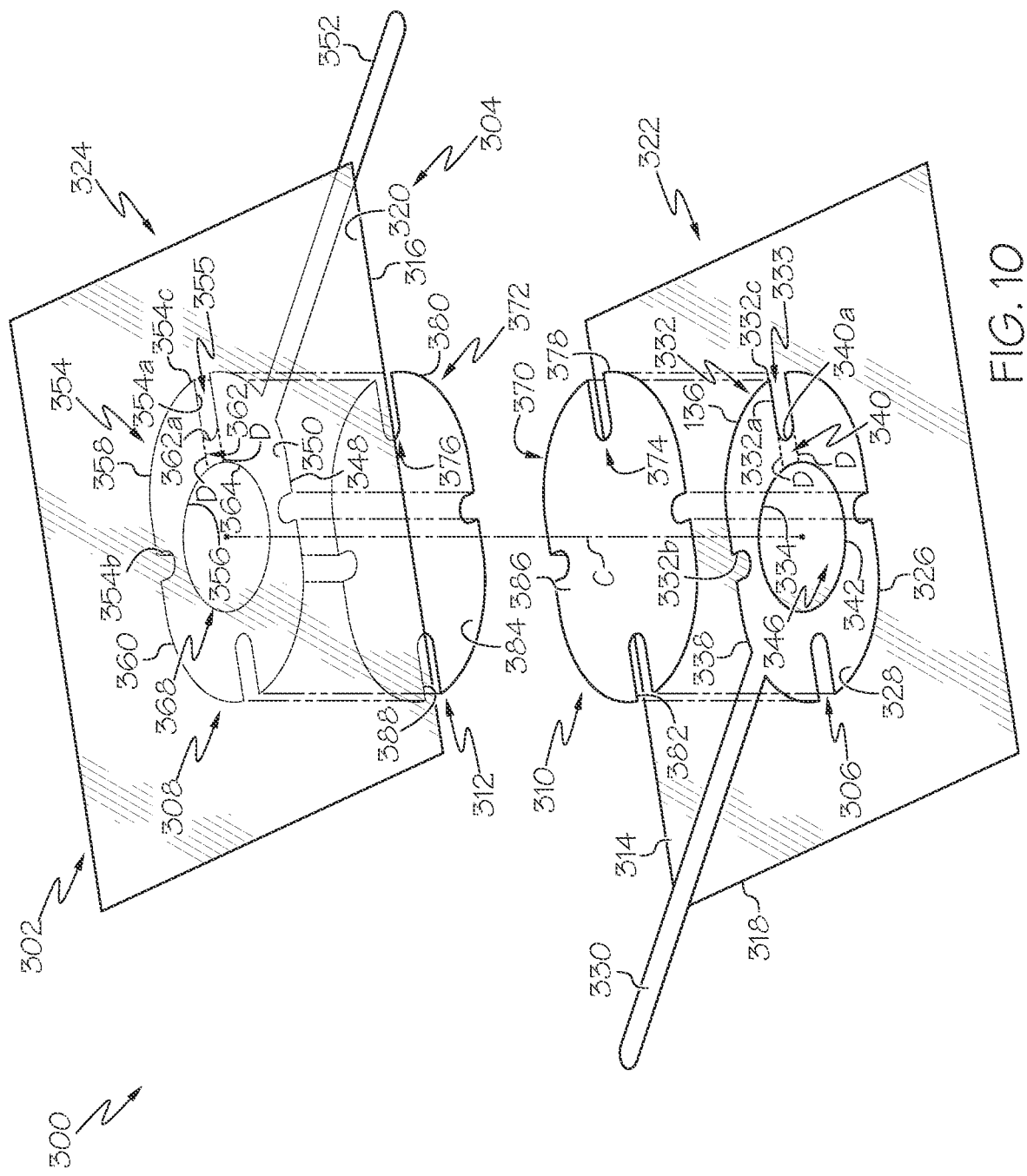
FIG. 10 schematically depicts an exploded view of another illustrative artificial muscle, according to one or more embodiments shown and described herein.
Figure 11:
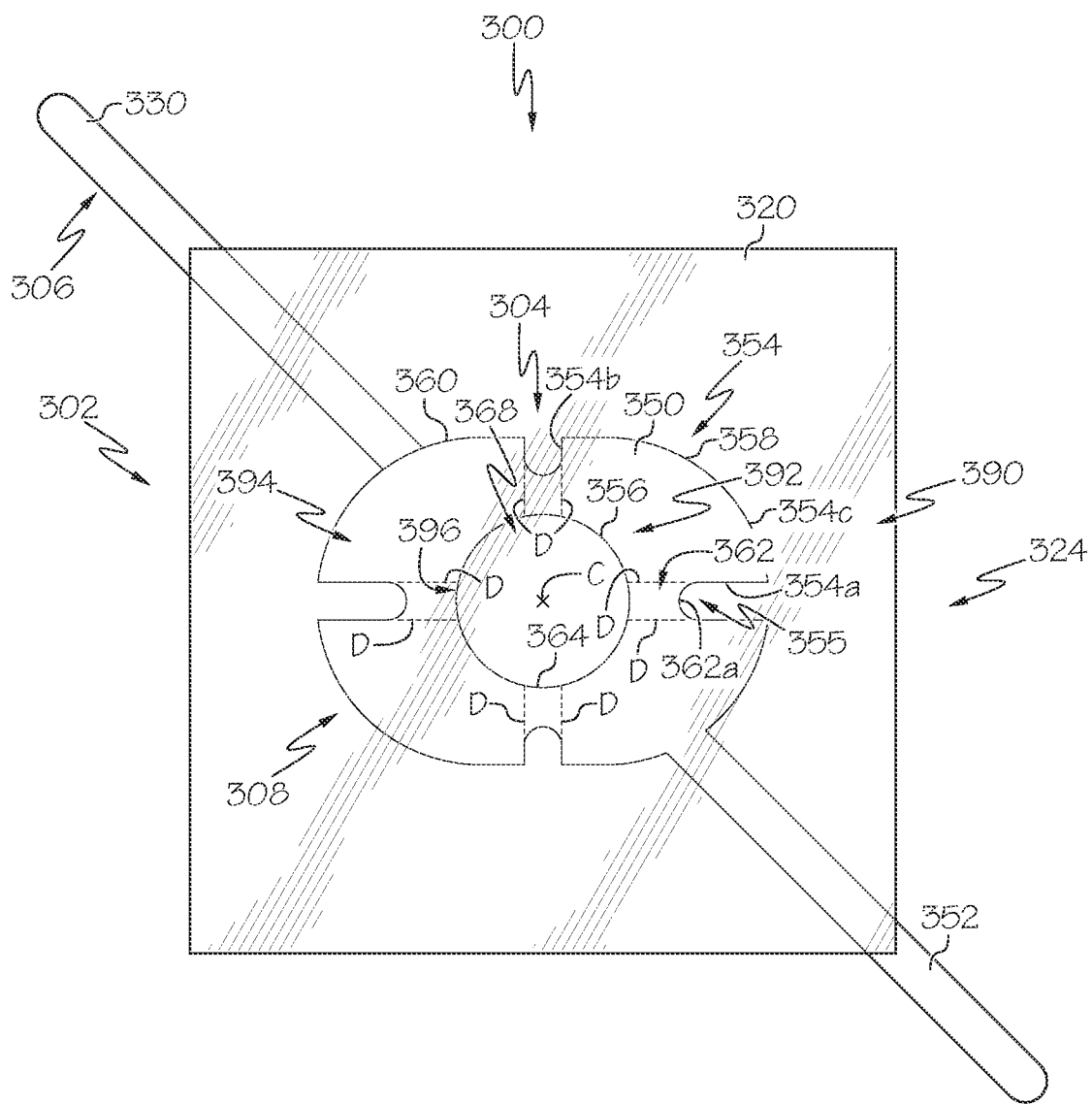
FIG. 11 schematically depicts a top view of the artificial muscle of FIG. 10, according to one or more embodiments shown and described herein.
Figure 12:
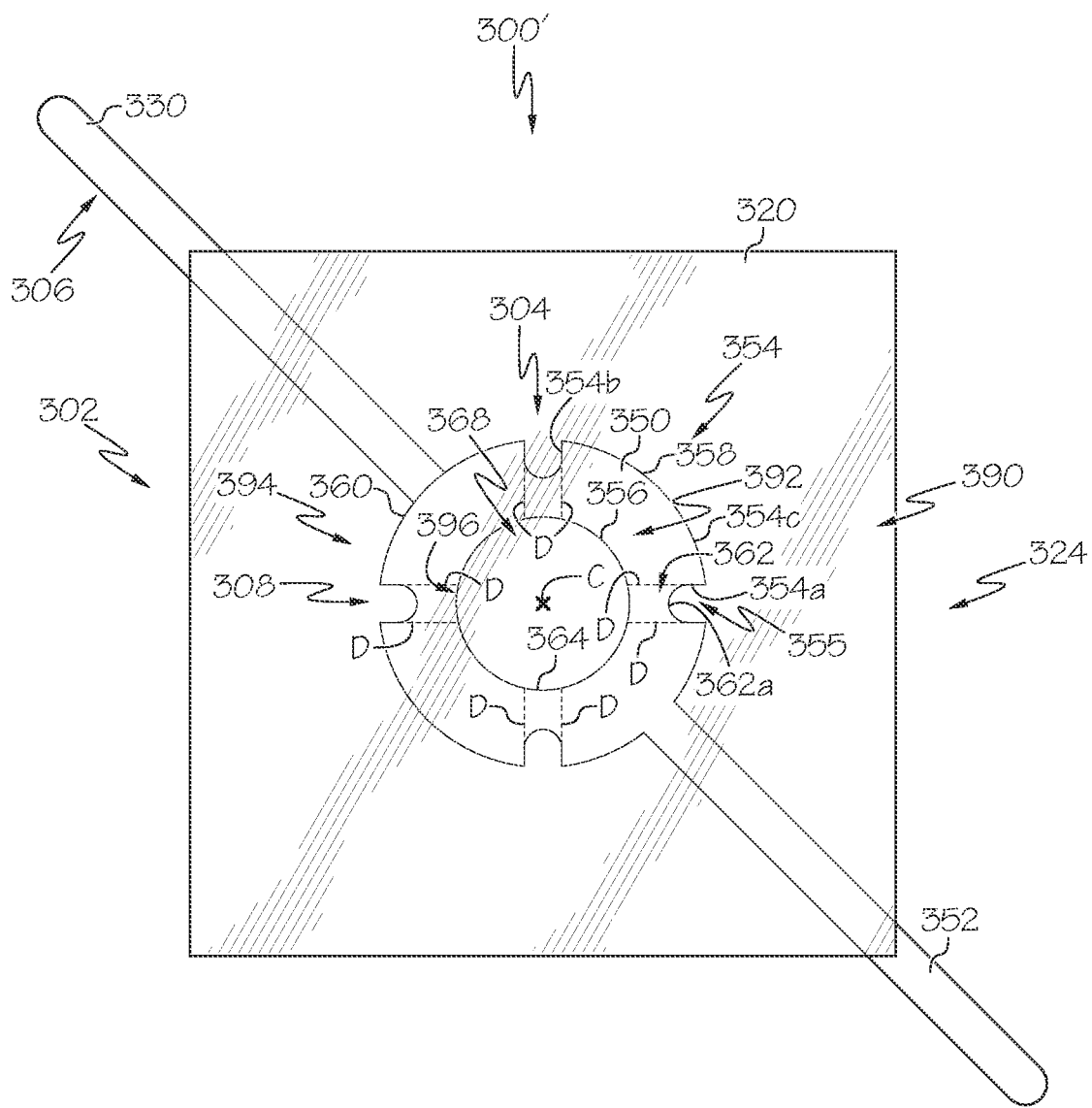
FIG. 12 schematically depicts a top view of another artificial muscle, according to one or more embodiments shown and described herein.

As shown in FIGS. 10-12, another embodiment of an artificial muscle 300 is illustrated. The artificial muscle 101 embodiment depicted in FIG. 1A may correspond to the artificial muscle embodiment 100 depicted in FIG. 3 and/or the artificial muscle embodiment 300 depicted in FIG. 10. It should be appreciated that the artificial muscle 300 includes similar structure as the artificial muscle 100 (FIGS. 3-9) and therefore operates similarly in operation to the artificial muscle 100 (FIGS. 3-9). Notably, the artificial muscle 300 includes fan portions 332 in place of the tab portions 132 discussed in relation to the artificial muscle 100. However, it should be understood that both the fan portions 332 of the artificial muscle 300 and the tab portions 132 are each generally a radially extending portion of an electrode of an artificial muscle, are positioned adjacent bridge portions, and provide a zipping functionality, as described above with respect to the artificial muscle 100. Indeed, these radially extending portions (e.g., tab portions and fan portions) each provide increased actuator power per unit volume, while minimizing buckling and rupture during operation.

Referring now to FIGS. 10 and 11, the artificial muscle 300 includes a housing 302, an electrode pair 304, including a first electrode 306 and a second electrode 308, fixed to opposite surfaces of the housing 302, a first electrical insulator layer 310 fixed to the first electrode 306, and a second electrical insulator layer 312 fixed to the second electrode 308. In some embodiments, the housing 302 is a one-piece monolithic layer including a pair of opposite inner surfaces, such as a first inner surface 314 and a second inner surface 316, and a pair of opposite outer surfaces, such as a first outer surface 318 and a second outer surface 320. In some embodiments, the first inner surface 314 and the second inner surface 316 of the housing 302 are heat-sealable. In other embodiments, the housing 302 may be a pair of individually fabricated film layers, such as a first film layer 322 and a second film layer 324. Thus, the first film layer 322 includes the first inner surface 314 and the first outer surface 318, and the second film layer 324 includes the second inner surface 316 and the second outer surface 320.

While reference may be made to the housing 302 including the first film layer 322 and the second film layer 324, as opposed to the one-piece housing. It should be understood that either arrangement is contemplated. In some embodiments, the first film layer 322 and the second film layer 324 generally include the same structure and composition. For example, in some embodiments, the first film layer 322 and the second film layer 324 each comprises biaxially oriented polypropylene.

The first electrode 306 and the second electrode 308 are each positioned between the first film layer 322 and the second film layer 324. In some embodiments, the first electrode 306 and the second electrode 308 are each aluminum-coated polyester such as, for example, Mylar®. In addition, one of the first electrode 306 and the second electrode 308 is a negatively charged electrode and the other of the first electrode 306 and the second electrode 308 is a positively charged electrode. For purposes discussed herein, either electrode 306, 308 may be positively charged so long as the other electrode 306, 308 of the artificial muscle 300 is negatively charged.

The first electrode 306 has a film-facing surface 326 and an opposite inner surface 328. The first electrode 306 is positioned against the first film layer 322, specifically, the first inner surface 314 of the first film layer 322. In addition, the first electrode 306 includes a first terminal 330 extending from the first electrode 306 past an edge of the first film layer 322 such that the first terminal 330 can be connected to a power supply to actuate the first electrode 306. Specifically, the terminal is coupled, either directly or in series, to a power supply and a controller of the actuation system 1300 (FIG. 13). Similarly, the second electrode 308 has a film-facing surface 348 and an opposite inner surface 350. The second electrode 308 is positioned against the second film layer 324, specifically, the second inner surface 316 of the second film layer 324. The second electrode 308 includes a second terminal 352 extending from the second electrode 308 past an edge of the second film layer 324 such that the second terminal 352 can be connected to a power supply and a controller of the actuation system 1300 (FIG. 13) to actuate the second electrode 308.

With respect now to the first electrode 306, the first electrode 306 includes two or more fan portions 332 extending radially from a center axis C of the artificial muscle 300. In some embodiments, the first electrode 306 includes only two fan portions 332 positioned on opposite sides or ends of the first electrode 306. In some embodiments, the first electrode 306 includes more than two fan portions 332, such as three, four, or five fan portions 332. In embodiments in which the first electrode 306 includes an even number of fan portions 332, the fan portions 332 may be arranged in two or more pairs of fan portions 332. As shown in FIG. 10, the first electrode 306 includes four fan portions 332. In this embodiment, the four fan portions 332 are arranged in two pairs of fan portions 332, where the two individual fan portions 332 of each pair are diametrically opposed to one another.

Each fan portion 332 has a first side edge 332a and an opposite second side edge 332b. As shown, the first terminal 330 extends from a second end 336 of one of the fan portions 332 and is integrally formed therewith. A channel 333 is at least partially defined by opposing side edges 332a. 332b of adjacent fan portions 332 and, thus, extends radially toward the center axis C. The channel 333 terminates at an end 340a of a bridge portion 340 interconnecting adjacent fan portions 332.

As shown in FIG. 10, dividing lines D are included to depict the boundary between the fan portions 332 and the bridge portions 340. The dividing lines D extend from the side edges 332a. 332b of the fan portions 332 to a first end 334 of the fan portions 332 collinear with the side edges 332a, 332b. It should be understood that dividing lines D are shown in FIG. 10 for clarity and that the fan portions 332 are integral with the bridge portions 340. The first end 334 of the fan portion 332, which extends between adjacent bridge portions 340, defines an inner length of the fan portion 332. Due to the geometry of the fan portion 332 tapering toward the center axis C between the first side edge 332a and the second side edge 332b, the second end 336 of the fan portion 332 defines an outer length of the fan portion 332 that is greater than the inner length of the fan portion 332.

Moreover, each fan portion 332 has a pair of corners 332c defined by an intersection of the second end 336 and each of the first side edge 332a and the second side edge 332b of the fan portion 332. In embodiments, the corners 332c are formed at an angle equal to or less than 90 degrees. In other embodiments, the corners 332c are formed at an acute angle.

As shown in FIG. 10, each fan portion 332 has a first side length defined by a distance between the first end 334 of the fan portion 332 and the second end 336 of the fan portion 332 along the first side edge 332a and the dividing line D that is collinear with the first side edge 332a. Each fan portion 332 also has a second side length defined by a distance between the first end 334 of the fan portion 332 and the second end 336 of the fan portion 332 along the second side edge 332b and the dividing line D that is collinear with the second side edge 332b. In embodiments, the first side length is greater than the second side length of the fan portion 332 such that the first electrode 306 has an ellipsoid geometry.

The second end 336, the first side edge 332a and the second side edge 332b of each fan portion 332, and the bridge portions 340 interconnecting the fan portions 332 define an outer perimeter 338 of the first electrode 306. In embodiments, a central opening 346 is formed within the first electrode 306 between the fan portions 332 and the bridge portions 340, and is coaxial with the center axis C. Each fan portion 332 has a fan length extending from a perimeter 342 of the central opening 346 to the second end 336 of the fan portion 332. Each bridge portion 340 has a bridge length extending from a perimeter 342 of the central opening 346 to the end 340a of the bridge portion 340, i.e., the channel 333. As shown, the bridge length of each of the bridge portions 340 is substantially equal to one another. Each channel 333 has a channel length defined by a distance between the end 340a of the bridge portion 340 and the second end of the fan portion 332. Due to the bridge length of each of the bridge portions 340 being substantially equal to one another and the first side length of the fan portions 332 being greater than the second side length of the fan portions 332, a first pair of opposite channels 333 has a channel length greater than a channel length of a second pair of opposite channels 333. As shown, a width of the channel 333 extending between opposing side edges 332a, 332b of adjacent fan portions 332 remains substantially constant due to opposing side edges 332a, 332b being substantially parallel to one another.

In embodiments, the central opening 346 has a radius of 2 centimeters (cm) to 5 cm. In embodiments, the central opening 346 has a radius of 3 cm to 4 cm. In embodiments, a total fan area of each of the fan portions 332 is equal to or greater than twice an area of the central opening 346. It should be appreciated that the ratio between the total fan area of the fan portions 332 and the area of the central opening 346 is directly related to a total amount of deflection of the first film layer 322 when the artificial muscle 300 is actuated. In embodiments, the bridge length is 20% to 50% of the fan length. In embodiments, the bridge length is 30% to 40% of the fan length. In embodiments in which the first electrode 306 does not include the central opening 346, the fan length and the bridge length may be measured from a perimeter of an imaginary circle coaxial with the center axis C.

Similar to the first electrode 306, the second electrode 308 includes two or more fan portions 354 extending radially from the center axis C of the artificial muscle 300. The second electrode 308 includes substantially the same structure as the first electrode 306 and, thus, includes the same number of fan portions 354. Specifically, the second electrode 308 is illustrated as including four fan portions 354. However, it should be appreciated that the second electrode 308 may include any suitable number of fan portions 354.

Each fan portion 354 of the second electrode 308 has a first side edge 354a and an opposite second side edge 354b. As shown, the second terminal 352 extends from a second end 358 of one of the fan portions 354 and is integrally formed therewith. A channel 355 is at least partially defined by opposing side edges 354a, 354b of adjacent fan portions 354 and, thus, extends radially toward the center axis C. The channel 355 terminates at an end 362a of a bridge portion 362 interconnecting adjacent fan portions 354.

As shown in FIG. 10, additional dividing lines D are included to depict the boundary between the fan portions 354 and the bridge portions 362. The dividing lines D extend from the side edges 354a. 354b of the fan portions 354 to the first end 356 of the fan portions 354 collinear with the side edges 354a, 354b. It should be understood that dividing lines D are shown in FIG. 10 for clarity and that the fan portions 354 are integral with the bridge portions 362. The first end 356 of the fan portion 354, which extends between adjacent bridge portions 362, defines an inner length of the fan portion 354. Due to the geometry of the fan portion 354 tapering toward the center axis C between the first side edge 354a and the second side edge 354b, the second end 358 of the fan portion 354 defines an outer length of the fan portion 354 that is greater than the inner length of the fan portion 354.

Moreover, each fan portion 354 has a pair of corners 354c defined by an intersection of the second end 358 and each of the first side edge 354a and the second side edge 354b of the fan portion 354. In embodiments, the corners 354c are formed at an angle equal to or less than 90 degrees. In other embodiments, the corners 354c are formed at an acute angle. During actuation of the artificial muscle 300, the corners 332c of the first electrode 306 and the corners 354c of the second electrode 308 are configured to be attracted to one another at a lower voltage as compared to the rest of the first electrode 306 and the second electrode 308. Thus, actuation of the artificial muscle 300 initially at the corners 332c, 354c results in the outer perimeter 338 of the first electrode 306 and the outer perimeter 360 of the second electrode 308 being attracted to one another at a lower voltage and reducing the likelihood of air pockets or voids forming between the first electrode 306 and the second electrode 308 after actuation of the artificial muscle 300.

As shown in FIGS. 10 and 11, in embodiments, the first side edge 354a of each fan portion 354 has a first side length defined by a distance between the first end 356 of the fan portion 354 and the second end 358 of the fan portion 354 along the first side edge 354a and the dividing line D that is collinear with the first side edge 354a. Each fan portion 354 also has a second side length defined by a distance between the first end 356 of the fan portion 354 and the second end 358 of the fan portion 354 along the second side edge 354b and the dividing line D that is collinear with the second side edge 354b. In embodiments, the first side length is greater than the second side length of the fan portion 354 such that the second electrode 308 has an ellipsoid geometry corresponding to the geometry of the first electrode 306.

The second end 358, the first side edge 354a and the second side edge 354b of each fan portion 354, and the bridge portions 362 interconnecting the fan portions 354 define an outer perimeter 360 of the second electrode 308. In embodiments, a central opening 368 is formed within the second electrode 308 between the fan portions 354 and the bridge portions 362, and is coaxial with the center axis C. Each fan portion 354 has a fan length extending from a perimeter 364 of the central opening 368 to the second end 358 of the fan portion 354. Each bridge portion 362 has a bridge length extending from the central opening 368 to the end 362a of the bridge portion 362, i.e., the channel 355. As shown, the bridge length of each of the bridge portions 362 is substantially equal to one another. Each channel 355 has a channel length defined by a distance between the end 362a of the bridge portion 362 and the second end of the fan portion 354. Due to the bridge length of each of the bridge portions 362 being substantially equal to one another and the first side length of the fan portions 354 being greater than the second side length of the fan portions 354, a first pair of opposite channels 355 has a channel length greater than a channel length of a second pair of opposite channels 355. As shown, a width of the channel 355 extending between opposing side edges 354a, 354b of adjacent fan portions 354 remains substantially constant due to opposing side edges 354a, 354b being substantially parallel to one another.

In embodiments, the central opening 368 has a radius of 2 cm to 5 cm. In embodiments, the central opening 368 has a radius of 3 cm to 4 cm. In embodiments, a total fan area of each of the fan portions 354 is equal to or greater than twice an area of the central opening 368. It should be appreciated that the ratio between the total fan area of the fan portions 354 and the area of the central opening 368 is directly related to a total amount of deflection of the second film layer 324 when the artificial muscle 300 is actuated. In embodiments, the bridge length is 20% to 50% of the fan length. In embodiments, the bridge length is 30% to 40% of the fan length. In embodiments in which the second electrode 308 does not include the central opening 368, the fan length and the bridge length may be measured from a perimeter of an imaginary circle coaxial with the center axis C.

As described herein, the first electrode 306 and the second electrode 308 each have a central opening 346, 368 coaxial with the center axis C. However, it should be understood that the first electrode 306 does not need to include the central opening 346 when the central opening 368 is provided within the second electrode 308. Alternatively, the second electrode 308 does not need to include the central opening 368 when the central opening 346 is provided within the first electrode 306.

Referring again to FIG. 10, the first electrical insulator layer 310 and the second electrical insulator layer 312 have a substantially ellipsoid geometry generally corresponding to the geometry of the first electrode 306 and the second electrode 308, respectively. Thus, the first electrical insulator layer 310 and the second electrical insulator layer 312 each have fan portions 370, 372 and bridge portions 374, 376 corresponding to like portions on the first electrode 306 and the second electrode 308. Further, the first electrical insulator layer 310 and the second electrical insulator layer 312 each have an outer perimeter 378, 380 corresponding to the outer perimeter 338 of the first electrode 306 and the outer perimeter 360 of the second electrode 308, respectively, when positioned thereon.

It should be appreciated that, in some embodiments, the first electrical insulator layer 310 and the second electrical insulator layer 312 generally include the same structure and composition. As such, in some embodiments, the first electrical insulator layer 310 and the second electrical insulator layer 312 each include an adhesive surface 382, 384 and an opposite non-sealable surface 386, 388, respectively. Thus, in some embodiments, the first electrical insulator layer 310 and the second electrical insulator layer 312 are each a polymer tape adhered to the inner surface 328 of the first electrode 306 and the inner surface 350 of the second electrode 308, respectively.

Referring now to FIG. 11, the artificial muscle 300 is shown in its assembled form with the first terminal 330 of the first electrode 306 and the second terminal 352 of the second electrode 308 extending past an outer perimeter of the housing 302, i.e., the first film layer 322 (FIG. 10) and the second film layer 324. The second electrode 308 is stacked on top of the first electrode 306 and, therefore, the first film layer 322 (FIG. 10) is not shown. In its assembled form, the first electrode 306, the second electrode 308, the first electrical insulator layer 310 (FIG. 10), and the second electrical insulator layer 312 (FIG. 10) are sandwiched between the first film layer 322 (FIG. 10) and the second film layer 324. The first film layer 322 (FIG. 10) is partially sealed to the second film layer 324 at an area surrounding the outer perimeter 338 (FIG. 10) of the first electrode 306 and the outer perimeter 360 of the second electrode 308. In some embodiments, the first film layer 322 (FIG. 10) is heat-sealed to the second film layer 324 (FIG. 10). Specifically, in some embodiments, the first film layer 322 (FIG. 13) is sealed to the second film layer 324 to define a sealed portion 390 surrounding the first electrode 306 and the second electrode 308. The first film layer 322 (FIG. 10) and the second film layer 324 may be sealed in any suitable manner, such as using an adhesive, heat sealing, vacuum sealing, or the like.

The first electrode 306, the second electrode 308, the first electrical insulator layer 310 (FIG. 10), and the second electrical insulator layer 312 (FIG. 10) provide a barrier that prevents the first film layer 322 (FIG. 10) from sealing to the second film layer 324, forming an unsealed portion 392. The unsealed portion 392 of the housing 302 includes an electrode region 394, in which the electrode pair 304 is provided, and an expandable fluid region 396, which is surrounded by the electrode region 394. The central openings 346 (FIG. 10), 368 of the first electrode 306 and the second electrode 308 define the expandable fluid region 396 and are arranged to be axially stacked on one another. Although not shown, the housing 302 may be cut to conform to the geometry of the electrode pair 304 and reduce the size of the artificial muscle 300, namely, the size of the sealed portion 390. A dielectric fluid is provided within the unsealed portion 392 and flows freely between the first electrode 306 and the second electrode 308

Referring now to FIG. 12, an alternative embodiment of an artificial muscle 300' is illustrated. It should be appreciated that the artificial muscle 300' is similar to the artificial muscle 300 described herein. As such, like structure is indicated with like reference numerals. The first electrode 306 and the second electrode 308 of the artificial muscle 300' have a circular geometry as opposed to the ellipsoid geometry of the first electrode 306 and the second electrode 308 of the artificial muscle 300 described herein. As shown in FIG. 12, with respect to the second electrode 308, a first side edge length of the first side edge 354a is equal to a second side edge length of the second side edge 354b. Accordingly, the channels 355 formed between opposing side edges 354a. 354b of the fan portions 354 each have an equal length. Although the first electrode 306 is hidden from view in FIG. 12 by the second electrode 308, it should be appreciated that the first electrode 306 also has a circular geometry corresponding to the geometry of the second electrode 308.

Referring again to FIGS. 10 and 11, actuation of the artificial muscle 300 will be discussed. In the non-actuated state, the first electrode 306 and the second electrode 308 are partially spaced apart from one another proximate the central openings 346, 368 thereof and the first end 334, 356 of the fan portions 332, 354. The second end 336, 358 of the fan portions 332, 354 remain in position relative to one another due to the housing 302 being sealed at the outer perimeter 338 of the first electrode 306 and the outer perimeter 360 of the second electrode 308. In the actuated state, the first electrode 306 and the second electrode 308 are brought into contact with and oriented parallel to one another to force the dielectric fluid 398 into the expandable fluid region 396. This causes the dielectric fluid 398 to flow through the central openings 346, 368 of the first electrode 306 and the second electrode 308 and inflate the expandable fluid region 396.

In the non-actuated state, a distance between the first end 334 of the fan portion 332 of the first electrode 306 and the first end 356 of the fan portion 354 of the second electrode 308 is greater than a distance between the second end 336 of the fan portion 332 of the first electrode 306 and the second end 358 of the fan portion 354 of the second electrode 308. This results in the electrode pair 304 zippering toward the expandable fluid region 396 when actuated. When actuated, the first electrode 306 and the second electrode 308 zipper toward one another from the second ends 336, 358 of the fan portions 332, 354 thereof, thereby pushing the dielectric fluid 398 into the expandable fluid region 396. When in the actuated state, the first electrode 306 and the second electrode 308 are parallel to one another. In the actuated state, the dielectric fluid 398 flows into the expandable fluid region 396 to inflate the expandable fluid region 396. As such, the first film layer 322 and the second film layer 324 expand in opposite directions.

Referring now to FIG. 13, an actuation system 1300 may be provided for operating the artificial muscle 100. The actuation system 1300 may comprise a controller 50, the one or more pressure sensors 80, an operating device 46, a power supply 48, a display device 42, network interface hardware 44, and a communication path 41 communicatively coupled these components, some or all of which may be disposed in the onboard control unit 40.

The controller 50 may comprise a processor 52 and a non-transitory electronic memory 54 to which various components are communicatively coupled. In some embodiments, the processor 52 and the non-transitory electronic memory 54 and/or the other components are included within a single device. In other embodiments, the processor 52 and the non-transitory electronic memory 54 and/or the other components may be distributed among multiple devices that are communicatively coupled. The controller 50 may include non-transitory electronic memory 54 that stores a set of machine-readable instructions. The processor 52 may execute the machine-readable instructions stored in the non-transitory electronic memory 54. The non-transitory electronic memory 54 may comprise RAM, ROM, flash memories, hard drives, or any device capable of storing machine-readable instructions such that the machine-readable instructions can be accessed by the processor 52. Accordingly, the actuation system 1300 described herein may be implemented in any computer programming language, as pre-programmed hardware elements, or as a combination of hardware and software components. The non-transitory electronic memory 54 may be implemented as one memory module or a plurality of memory modules. In some embodiments, the non-transitory electronic memory 54 includes instructions for executing the functions of the actuation system 1300. The instructions may include instructions for operating/actuating the artificial muscle 100.

The processor 52 may be any device capable of executing machine-readable instructions. For example, the processor 52 may be an integrated circuit, a microchip, a computer, or any other computing device. The non-transitory electronic memory 54 and the processor 52 are coupled to the communication path 41 that provides signal interconnectivity between various components and/or modules of the actuation system 1300. Accordingly, the communication path 41 may communicatively couple any number of processors with one another, and allow the modules coupled to the communication path 41 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 13, the communication path 41 communicatively couples the processor 52 and the non-transitory electronic memory 54 of the controller 50 with a plurality of other components of the actuation system 1300. For example, the actuation system 1300 depicted in FIG. 13 includes the processor 52 and the non-transitory electronic memory 54 communicatively coupled with the pressure sensor 80, operating device 46, and the power supply 48.

The operating device 46 allows for a user to control operation of the artificial muscle 100. In some embodiments, the operating device 46 may be a switch, toggle, button, or any combination of controls to provide user operation. The operating device 46 is coupled to the communication path 41 such that the communication path 41 communicatively couples the operating device 46 to other modules of the actuation system 1300. The operating device 46 may provide a user interface for receiving user instructions as to a specific operating configuration of the artificial muscle 100, such as an amount desired actuation.

The power supply 48 (e.g., battery) provides power to the artificial muscle 100. In some embodiments, the power supply 48 is a rechargeable direct current power source. It is to be understood that the power supply 48 may be a single power supply or battery for providing power to the artificial muscle 100. A power adapter (not shown) may be provided and electrically coupled via a wiring harness or the like for providing power to the artificial muscle 100 via the power supply 48. Indeed, the power supply 48 is a device that can receive power at one level (e.g., one voltage, power level, or current) and output power at a second level (e.g., a second voltage, power level, or current).

In some embodiments, the actuation system 1300 also includes a display device 42. The display device 42 is coupled to the communication path 41 such that the communication path 41 communicatively couples the display device 42 to other modules of the actuation system 1300. The display device 42 may output a notification in response to an actuation state of the artificial muscle 100 or indication of a change in the actuation state of the artificial muscle 100. The display device 42 may be a touchscreen that, in addition to providing optical information, detects the presence and location of a tactile input upon a surface of or adjacent to the display device 42. Accordingly, the display device 42 may include the operating device 46 and receive mechanical input directly upon the optical output provided by the display device 42. For example, a user may be able to specify a desired actuation pressure value.

In some embodiments, the actuation system 1300 includes network interface hardware 44 for communicatively coupling the actuation system 1300 to a portable device 70 via a network 60. The portable device 70 may include, without limitation, a smartphone, a tablet, a personal media player, or any other electric device that includes wireless communication functionality. The portable device 70 may correspond to an infotainment device, or any other type of device capable of communicating with the network interface hardware 44, utilizing Wi-Fi, Bluetooth, and/or any other suitable communication protocol. It is to be appreciated that, when provided, the portable device 70 may serve to provide user commands to the controller 50, instead of the operating device 46. As such, a user may be able to control or set a program for controlling an artificial muscle 100 utilizing the controls of the operating device 46. Thus, the artificial muscle 100 may be controlled remotely via the portable device 70 wirelessly communicating with the controller 50 via the network 60. For example, the user may be able to specify a desired pressure value. The portable device 70 may also receive and display pressure readings from one or more pressure sensors 80 associated with the artificial muscle 100.

It should now be understood that embodiments described herein are directed to an artificial muscle having an electrode in contact with a composite electrical insulating layered structure that utilizes $TiO_2$ nanoparticles, which may be arranged within a layer. The $TiO_2$ nanoparticles may be located within one or more acrylic adhesives surrounded by a biaxially oriented polypropylene film in contact with an electrode. The $TiO_2$ nanoparticles significantly increase the force output of the artificial muscle, thus creating more force output with the same size actuator and the same operating voltage.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An artificial muscle comprising:
   a housing comprising an electrode region and an expandable liquid region;
   a dielectric liquid housed within the housing;
   an electrode pair positioned in the electrode region of the housing, the electrode pair comprising a first electrode and a second electrode, wherein the electrode pair is configured to actuate between a non-actuated state and an actuated state such that actuation from the non-actuated state to the actuated state directs the dielectric liquid into the expandable liquid region, expanding the expandable liquid region; and
   a composite electrical insulating layered structure in contact with at least one of the first electrode or the second electrode, wherein the composite electrical insulating layered structure comprises:
      an electrical insulator layer residing between and in contact with a plurality of adhesive surfaces;
      the adhesive surfaces located between one or more flexible electrical insulators; and
      the one or more flexible electrical insulators of which at least one is directly affixed to one of the first electrode and the second electrode.

2. The artificial muscle of claim 1, wherein the electrical insulator layer comprises titanium dioxide nanoparticles.

3. The artificial muscle of claim 2, wherein the titanium dioxide nanoparticles are doped with 1% manganese.

4. The artificial muscle of claim 1, wherein the one or more flexible electrical insulators comprises a biaxially oriented polypropylene film.

5. The artificial muscle of claim 1, wherein the adhesive surfaces comprise an acrylic adhesive.

6. The artificial muscle of claim 1, wherein at least one of the adhesive surfaces comprises titanium dioxide nanoparticles.

7. The artificial muscle of claim 6, wherein the at least one of the adhesive surfaces comprises titanium dioxide nanoparticles in a concentration that increases with proximity to the electrical insulator layer.

8. The artificial muscle of claim 1, wherein the electrical insulator layer has a thickness in a range of 10-15 µm.

9. The artificial muscle of claim 1, wherein the electrical insulator layer has a thickness in a range >0.1 µm and <100 µm.

10. The artificial muscle of claim 1, wherein a value of an increase in thickness of the electrical insulator layer in µm, squared, is less than the corresponding increase in a dielectric constant.

11. The artificial muscle of claim 1, wherein:
    the first electrode and the second electrode each comprises two or more radially extending portions and two or more bridge portions;
    each of the two or more bridge portions interconnects adjacent radially extending portions; and
    at least one of the first electrode and the second electrode comprises a central opening positioned between the two or more radially extending portions and encircling the expandable liquid region.

12. The artificial muscle of claim 11, wherein the two or more radially extending portions comprise two or more fan portions, wherein:
    each fan portion includes a first end having an inner length, a second end having an outer length, a first side edge extending from the second end, and a second side edge extending from the second end, wherein the outer length is greater than the inner length;
    each bridge portion interconnects adjacent fan portions at the first end of the adjacent fan portions; and
    at least one of the first electrode and the second electrode comprises a central opening positioned between the two or more fan portions and encircling the expandable liquid region.

13. The artificial muscle of claim 11, wherein:
    the two or more radially extending portions comprise two or more tab portions and two or more bridge portions;
    each of the two or more bridge portions interconnects adjacent tab portions; and
    at least one of the first electrode and the second electrode comprises a central opening positioned between the two or more tab portions and encircling the expandable liquid region.

14. An artificial muscle comprising:
    a housing comprising an electrode region and an expandable liquid region;
    a dielectric liquid housed within the housing;
    an electrode pair positioned in the electrode region of the housing, the electrode pair comprising a first electrode and a second electrode, wherein the electrode pair is configured to actuate between a non-actuated state and an actuated state such that actuation from the non-actuated state to the actuated state directs the dielectric liquid into the expandable liquid region, expanding the expandable liquid region; and
    a composite electrical insulating layered structure in contact with at least one of the first electrode or the second electrode, wherein the composite electrical insulating layered structure comprises:
       a plurality of electrical insulator nanoparticles located within a subset of an adhesive surface, the adhesive surface including a first material, the plurality of electrical insulator nanoparticles includes a second material;

the adhesive surface located between one or more flexible electrical insulators; and the one or more flexible electrical insulators of which at least one is directly affixed to one of the first electrode and the second electrode.

15. The artificial muscle of claim 14, wherein the electrical insulator nanoparticles comprise titanium dioxide nanoparticles.

16. The artificial muscle of claim 14, wherein the adhesive surface comprises an acrylic adhesive.

17. The artificial muscle of claim 14, wherein each flexible electrical insulator comprises a biaxially oriented polypropylene film.

18. The artificial muscle of claim 14, wherein:

the first electrode and the second electrode each comprise two or more radially extending portions and two or more bridge portions;

each of the two or more bridge portions interconnects adjacent radially extending portions; and at least one of the first electrode and the second electrode comprises a central opening positioned between the two or more radially extending portions and encircling the expandable liquid region.

19. An artificial muscle comprising:

a housing comprising an electrode region and an expandable liquid region;

a dielectric liquid housed within the housing;

an electrode pair positioned in the electrode region of the housing, the electrode pair comprising a first electrode and a second electrode, wherein the electrode pair is configured to actuate between a non-actuated state and an actuated state such that actuation from the non-actuated state to the actuated state directs the dielectric liquid into the expandable liquid region, expanding the expandable liquid region; and a composite electrical insulating layered structure in contact with at least one of the first electrode or the second electrode, wherein the composite electrical insulating layered structure comprises:

an electrical insulator layer comprising titanium dioxide nanoparticles, wherein the electrical insulator layer has a thickness in a range of 10-15 μm and is surrounded by acrylic adhesives;

the acrylic adhesives located within one or more biaxially oriented polypropylene films; and the one or more biaxially oriented polypropylene films of which at least one is directly affixed to one of the first electrode and the second electrode.

20. An artificial muscle of claim 19, wherein at least one of the acrylic adhesives comprises titanium dioxide nanoparticles in a concentration that increases with proximity to the electrical insulator layer.

* * * * *

UNITED STATES PATENT AND TRADEMARK OFFICE
CERTIFICATE OF CORRECTION

PATENT NO. : 12,031,558 B2
APPLICATION NO. : 17/529531
DATED : July 9, 2024
INVENTOR(S) : Max Herzog et al.

It is certified that error appears in the above-identified patent and that said Letters Patent is hereby corrected as shown below:

In the Specialization

In Column 5, Line(s) 10, delete "111.A" and insert --111A--, therefor.

In Column 6, Line(s) 10, delete "10 may" and insert --100 may--, therefor.

In Column 6, Line(s) 21, delete "11 IC", insert --111C--.

In Column 11, Line(s) 6, after "E. Acome", delete "." and insert --,--, therefor.

In Column 14, Line(s) 37, delete "332a. 332b" and insert --332a, 332b--, therefor.

Signed and Sealed this
Twentieth Day of August, 2024

Katherine Kelly Vidal
*Director of the United States Patent and Trademark Office*